US009846089B2

(12) United States Patent
Yao

(10) Patent No.: US 9,846,089 B2
(45) Date of Patent: Dec. 19, 2017

(54) CALORIMETER AND METHOD FOR DESIGNING CALORIMETER

(71) Applicant: NATIONAL UNIVERSITY CORPORATION KYOTO INSTITUTE OF TECHNOLOGY, Kyoto-shi, Kyoto (JP)

(72) Inventor: Haruhiko Yao, Kyoto (JP)

(73) Assignee: NATIONAL UNIVERSITY CORPORATION KYOTO INSTITUTE OF TECHNOLOGY, Kyoto-shi (JP)

(*) Notice: Subject to any disclaimer, the term of this patent is extended or adjusted under 35 U.S.C. 154(b) by 362 days.

(21) Appl. No.: 14/420,094

(22) PCT Filed: Aug. 7, 2013

(86) PCT No.: PCT/JP2013/071437
§ 371 (c)(1),
(2) Date: Feb. 6, 2015

(87) PCT Pub. No.: WO2014/024945
PCT Pub. Date: Feb. 13, 2014

(65) Prior Publication Data
US 2015/0219574 A1 Aug. 6, 2015

(30) Foreign Application Priority Data

Aug. 7, 2012 (JP) ................. 2012-174754

(51) Int. Cl.
*G01K 17/04* (2006.01)
*H01L 35/32* (2006.01)
(Continued)

(52) U.S. Cl.
CPC ........... *G01K 17/04* (2013.01); *G01N 25/482* (2013.01); *H01L 35/32* (2013.01)

(58) Field of Classification Search
CPC ..................................... G01K 17/04
See application file for complete search history.

(56) References Cited

U.S. PATENT DOCUMENTS 5,824,561 A 10/1998 Kishi et al.
6,329,696 B1 * 12/2001 Tanaka .................. G01F 1/6845
257/417
(Continued)

FOREIGN PATENT DOCUMENTS

JP 50-66282 A 6/1975
JP 64-10135 A 1/1989
(Continued)

OTHER PUBLICATIONS

Mattsson et al ("Thermal Simulation and Design Optimization of a Thermopile Infrared Detector With an SU-8 Membrane". Journal of Micromechanics and Microengineering 19.5 (2009): 055016).*
(Continued)

*Primary Examiner* — Minh Phan
*Assistant Examiner* — Leon W Rhodes, Jr.
(74) *Attorney, Agent, or Firm* — Westerman, Hattori, Daniels & Adrian,

(57) ABSTRACT

There is provided a calorimeter. Heat flows in and out of the sample via a thermoelectric module. The thermoelectric module is so constituted that a pair of a P-type thermoelectric element and an N-type thermoelectric element is disposed between substrates, and the pair of the thermoelectric elements are connected in n pairs so that the P-type thermoelectric elements and the N-type thermoelectric element are arranged alternately in π-shape; a calorimetric sensitivity of the thermoelectric module of a thermal conductance surrounding thermoelectric module and a thermal conductance between substrates of the thermoelectric modules and a noise based on an electric resistance of the thermoelectric module depend on an L/A ratio of the thermoelectric ele-
(Continued)

ment constituting the thermoelectric module and the number n of the pairs of the thermoelectric elements, where the L/A ratio is 6 mm$^{-1}$ or more, and the number n of the pairs is 4 or more.

5 Claims, 34 Drawing Sheets

(51) Int. Cl.
   *G01N 25/48* (2006.01)
   *G01N 25/20* (2006.01)

(56) References Cited

U.S. PATENT DOCUMENTS

| | | | |
|---|---|---|---|
| 6,335,478 B1 * | 1/2002 | Chou | ............... H01L 35/00 136/201 |
| 6,597,051 B2 * | 7/2003 | Lubomirsky | ............. G01J 5/12 257/431 |
| 2009/0007952 A1 | 1/2009 | Kondoh et al. | |

FOREIGN PATENT DOCUMENTS

| | | |
|---|---|---|
| JP | 6410135 A * | 1/1989 |
| JP | 5-223764 A | 8/1993 |
| JP | 8-97472 A | 4/1996 |
| JP | 10-125963 A | 5/1998 |
| JP | 2004-20509 A | 1/2004 |
| JP | 2012-38980 A | 2/2012 |
| WO | 2006/043514 A1 | 4/2006 |

OTHER PUBLICATIONS

International Search Report dated Oct. 22, 2013, issued in corresponding application No. PCT/JP2013/071437.

* cited by examiner

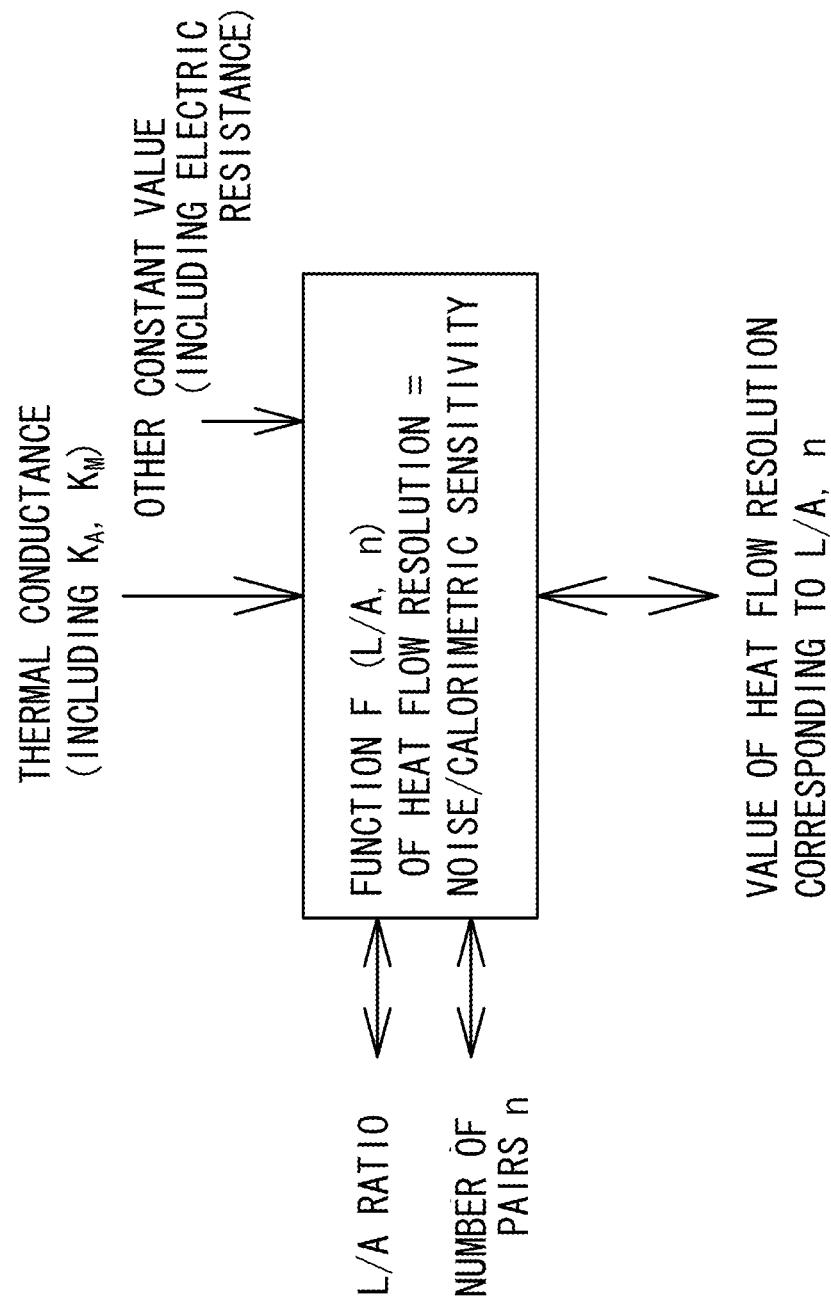
[Fig. 1]

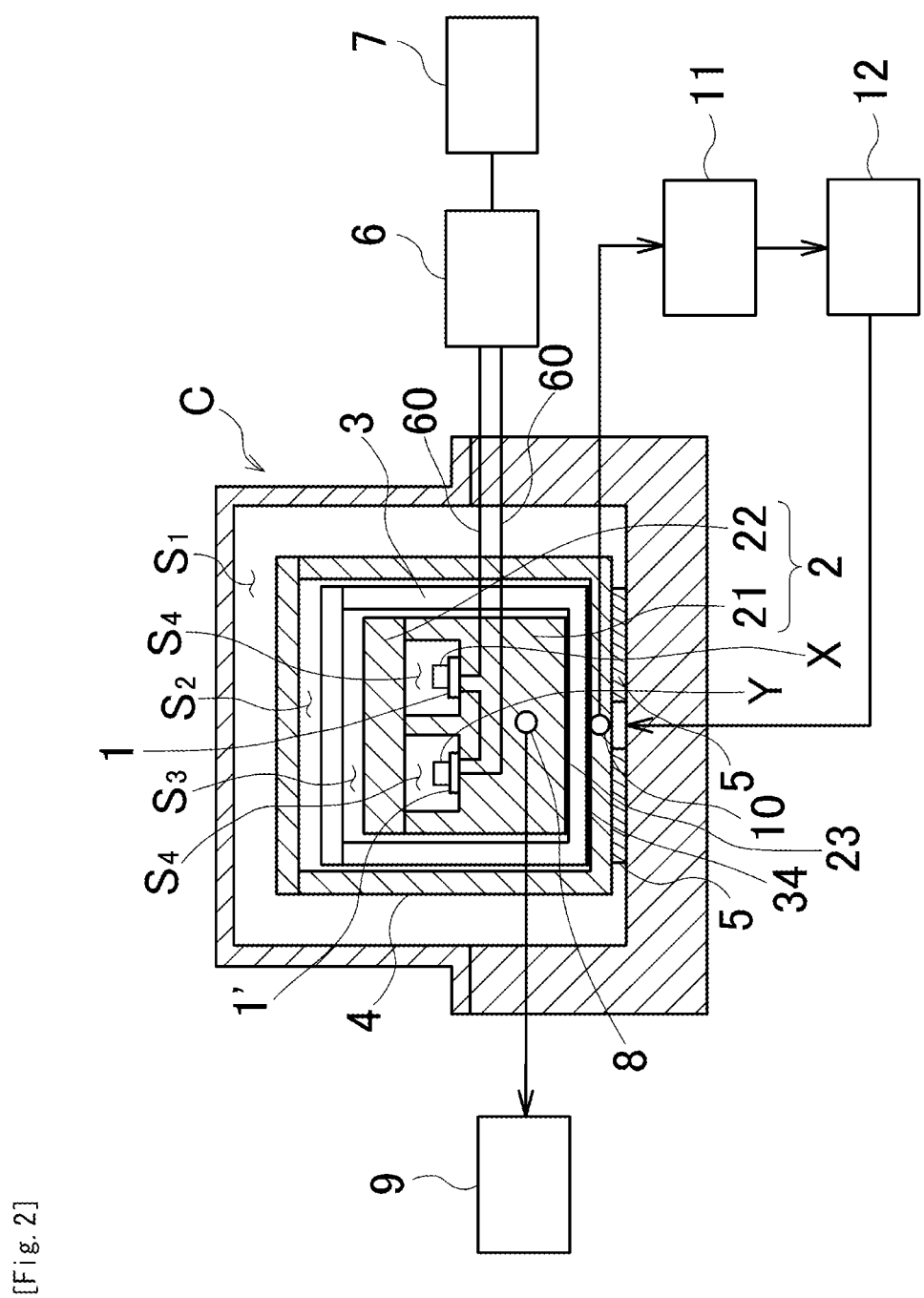
[Fig. 2]

[Fig. 3]
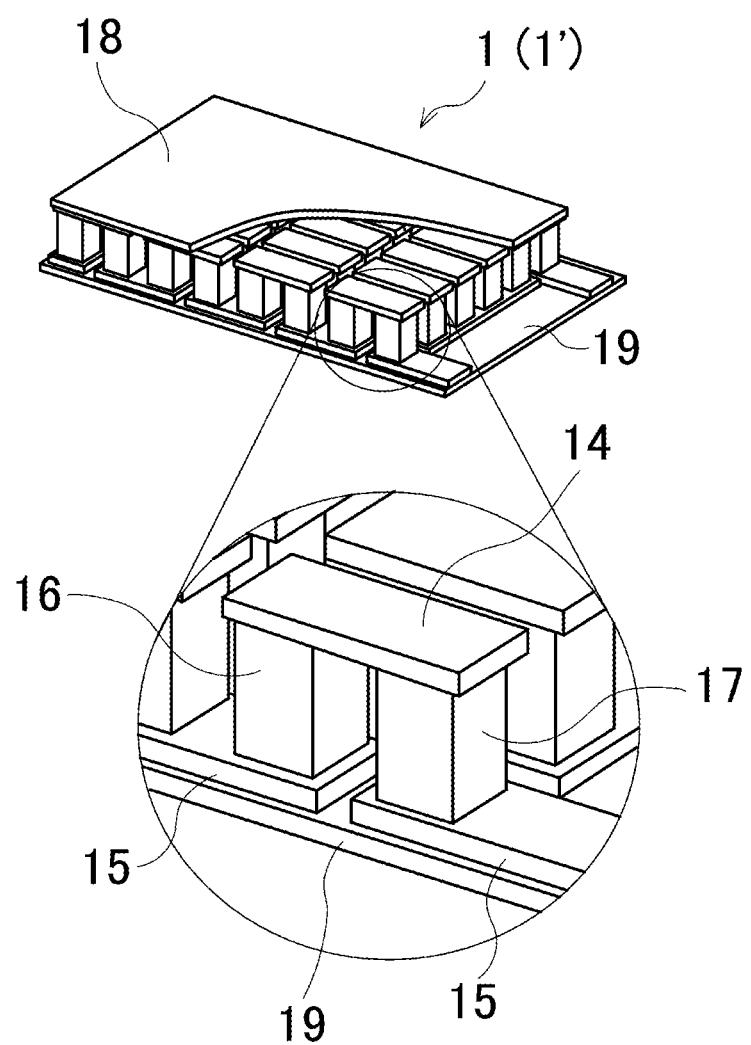

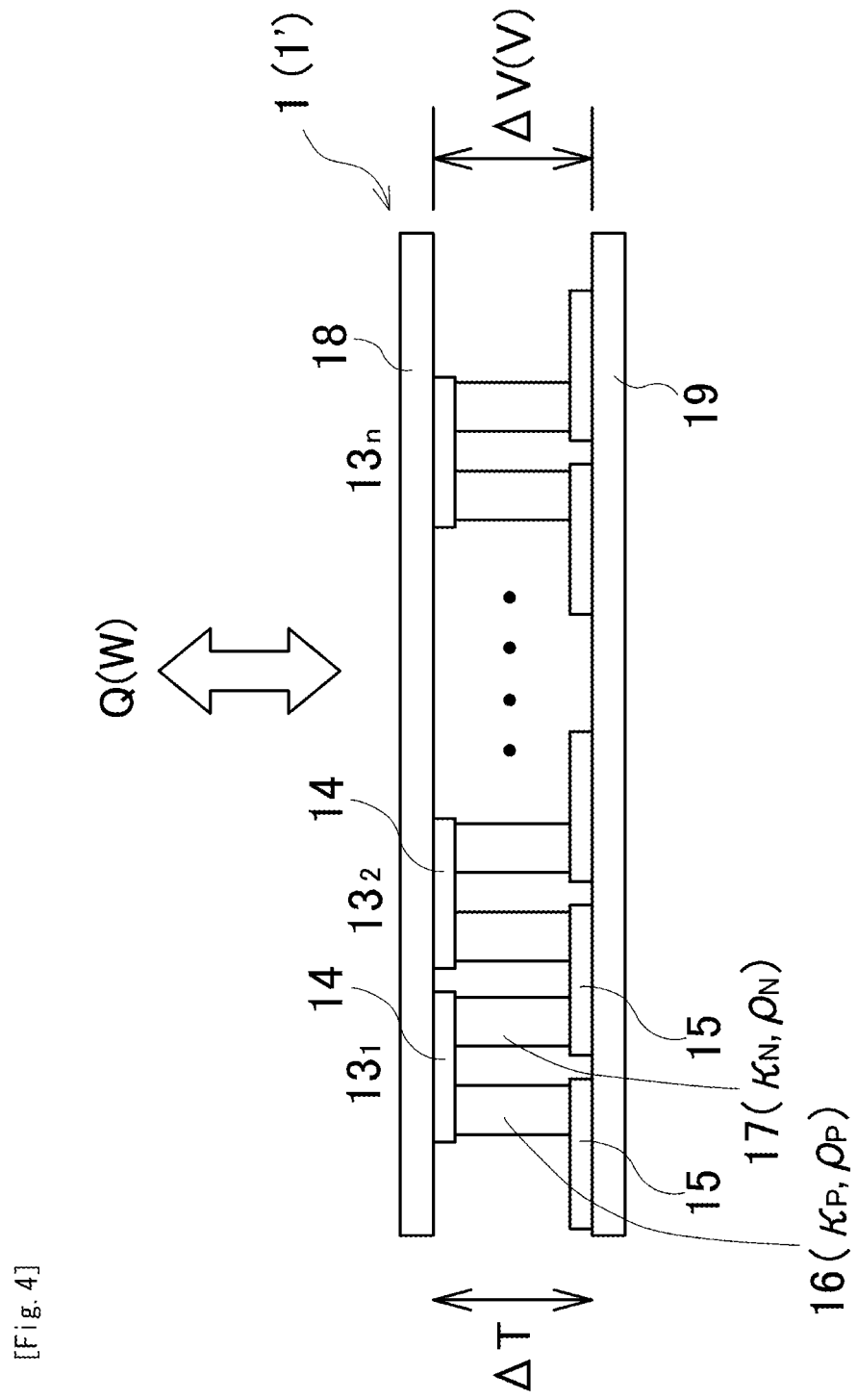
[Fig. 4]

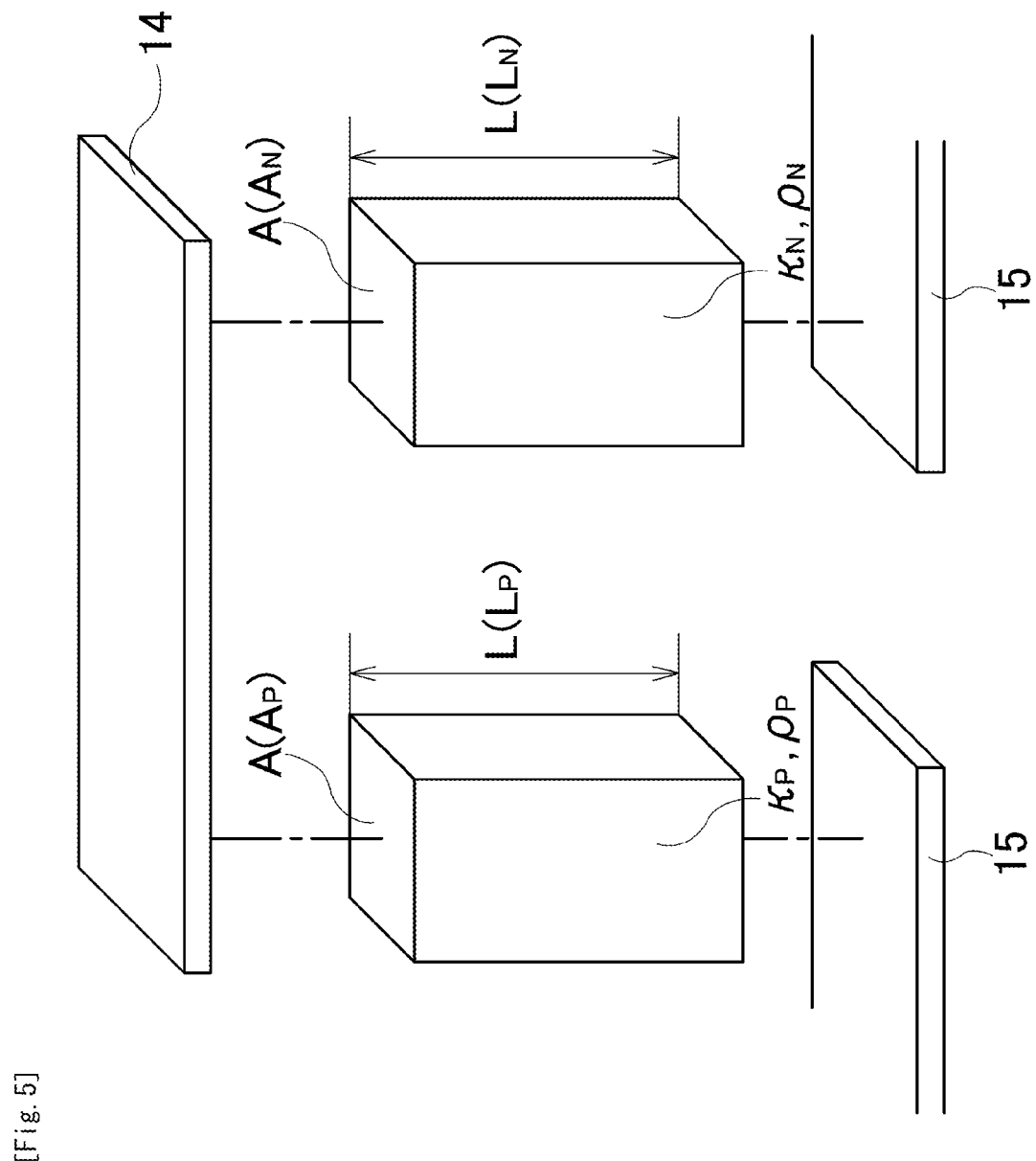

[Fig. 6]
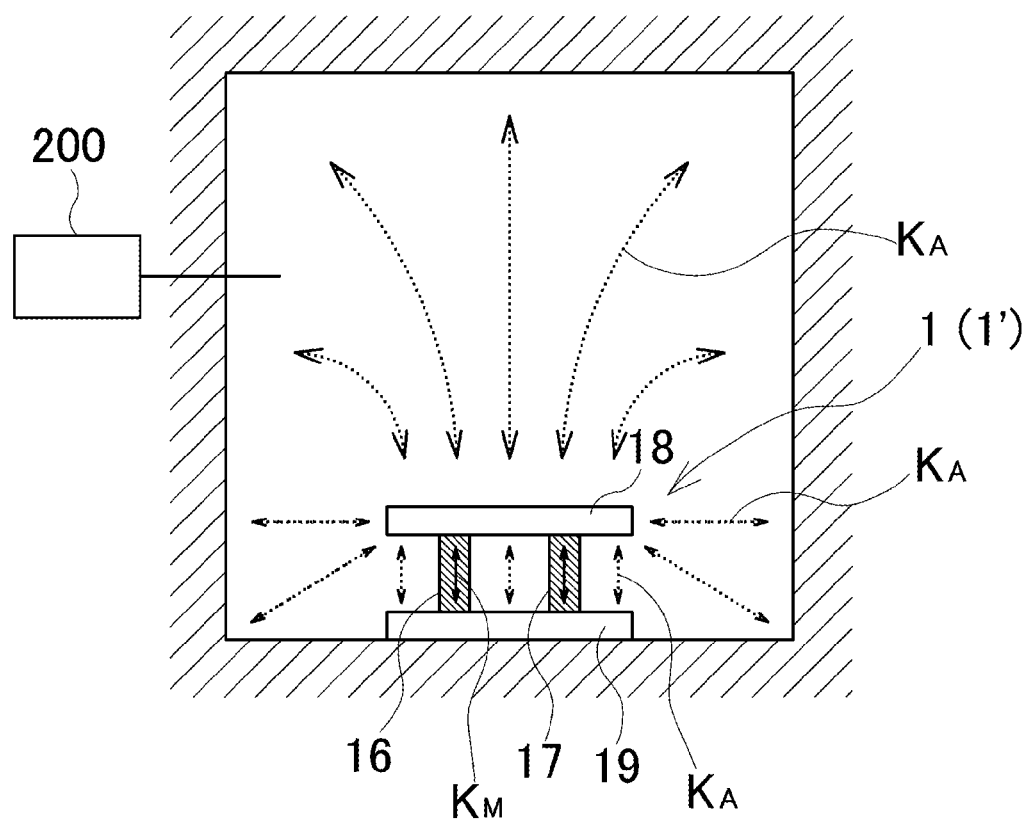

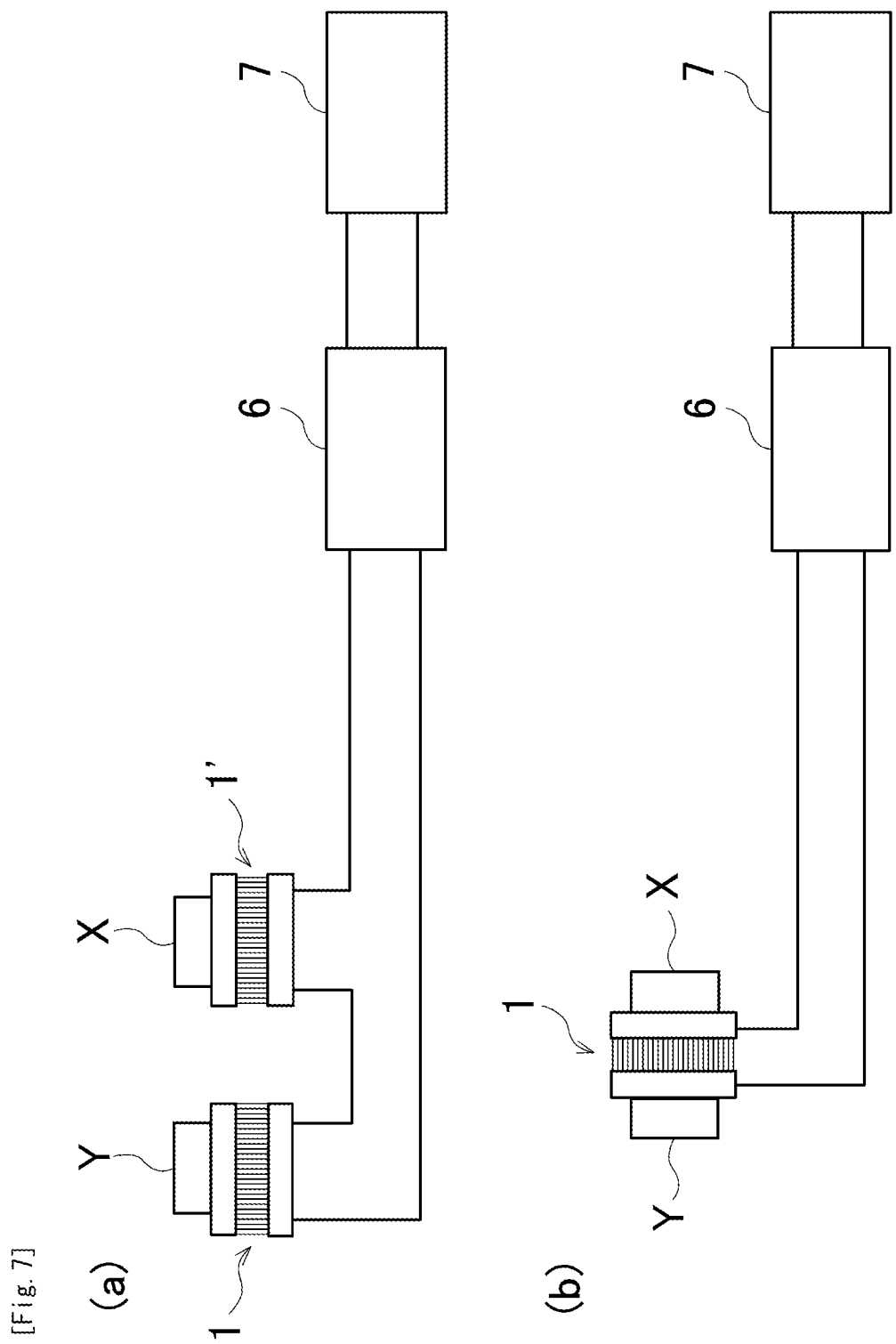

[Fig. 8]
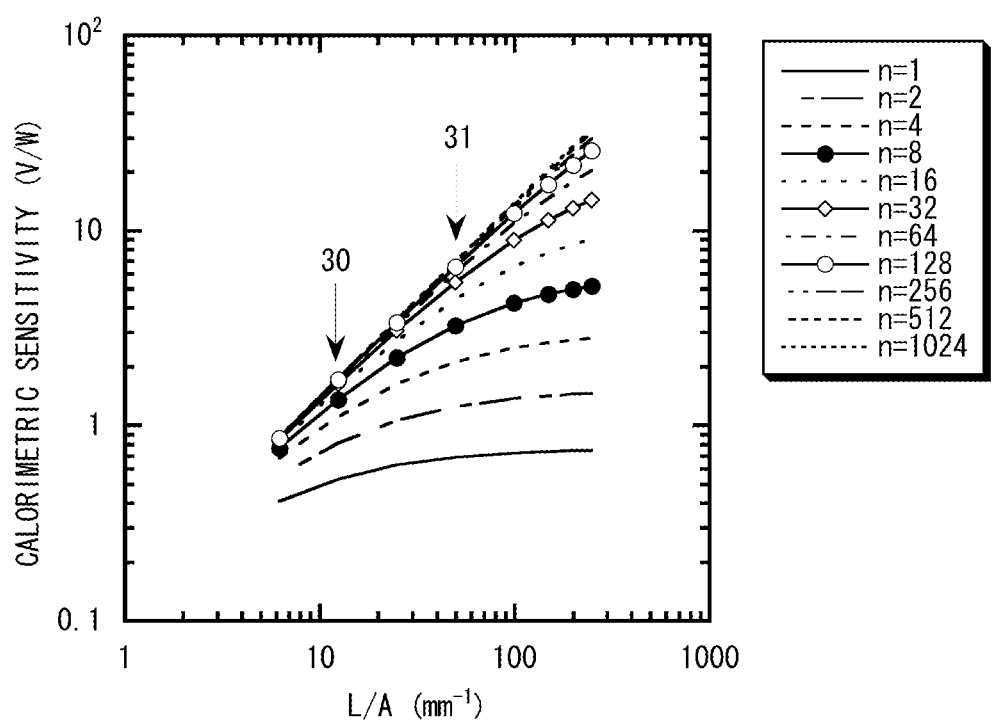
30: PROTO-TYPED THERMOELECTRIC MODULE
31: PROTO-TYPED THERMOELECTRIC MODULE

[Fig. 9]
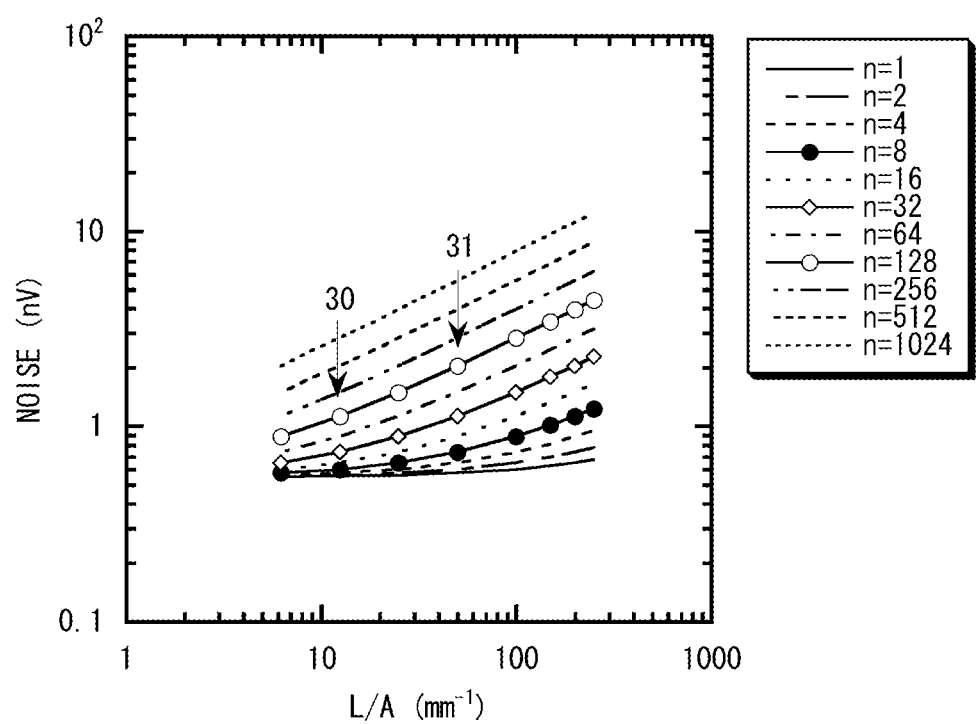

[Fig. 10]
(a)
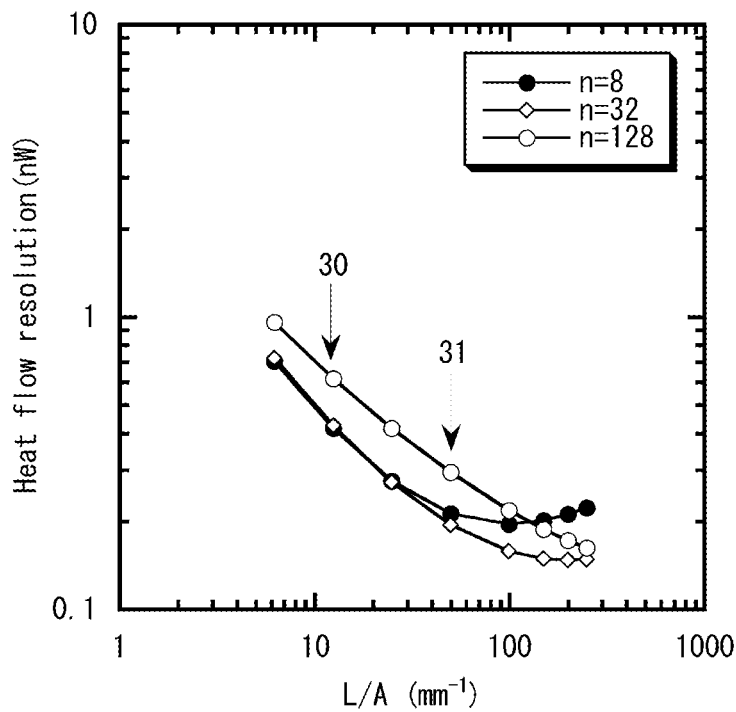
(b)
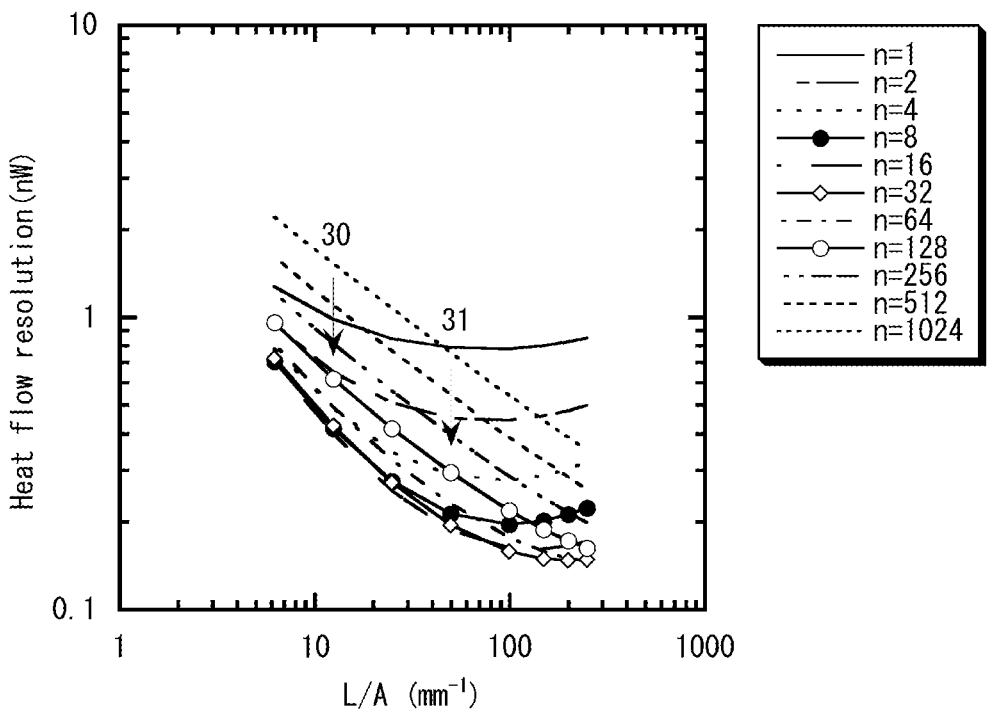

[Fig. 11]

| NUMBER OF PAIRS | NOISE | |
|---|---|---|
| | L/A(mm⁻¹) | |
| | 12.5 | 50 |
| 8 | ±0.8nV | ±2.9nV |
| 32 | ±1.1nV | ±1.3nV |
| 128 | ±1.1nV | ±4.7nV |

[Fig. 12]

HEAT FLOW RESOLUTION

| NUMBER OF PAIRS | L/A(mm$^{-1}$) | |
|---|---|---|
| | 12.5 | 50 |
| 8 | ±0.53nW | ±0.88nW |
| 32 | ±0.64nW | ±0.24nW |
| 128 | ±0.61nW | ±0.72nW |

[Fig. 13]
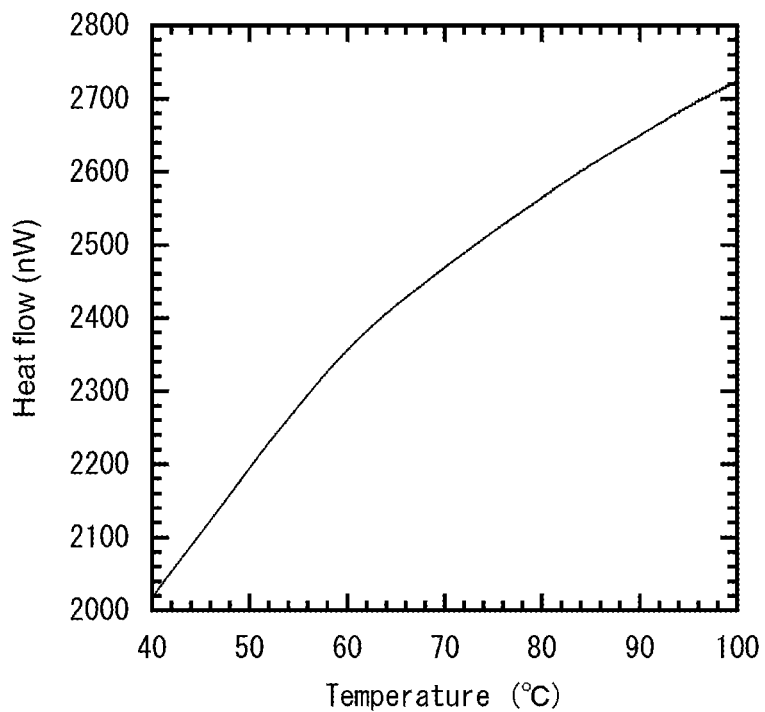
[Fig. 14]
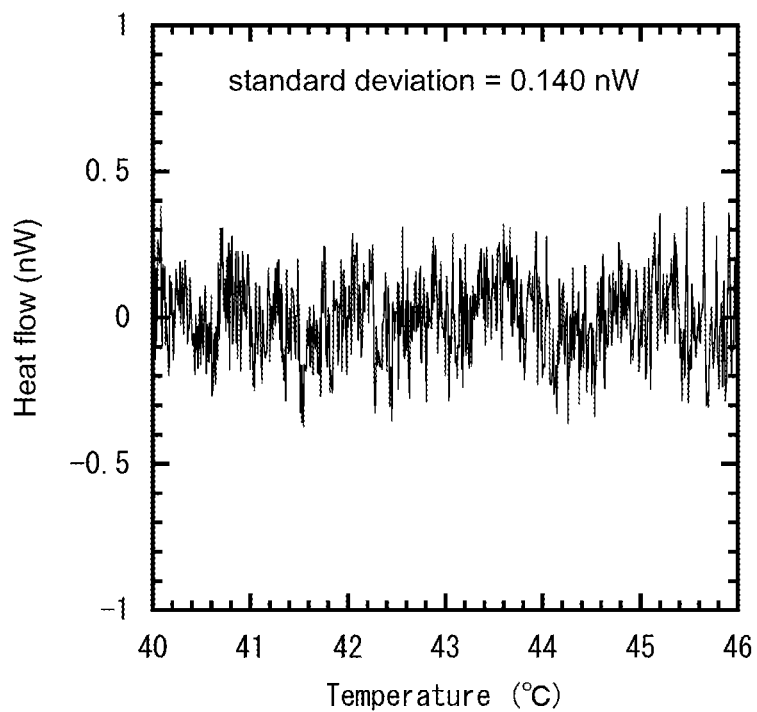

[Fig. 15]
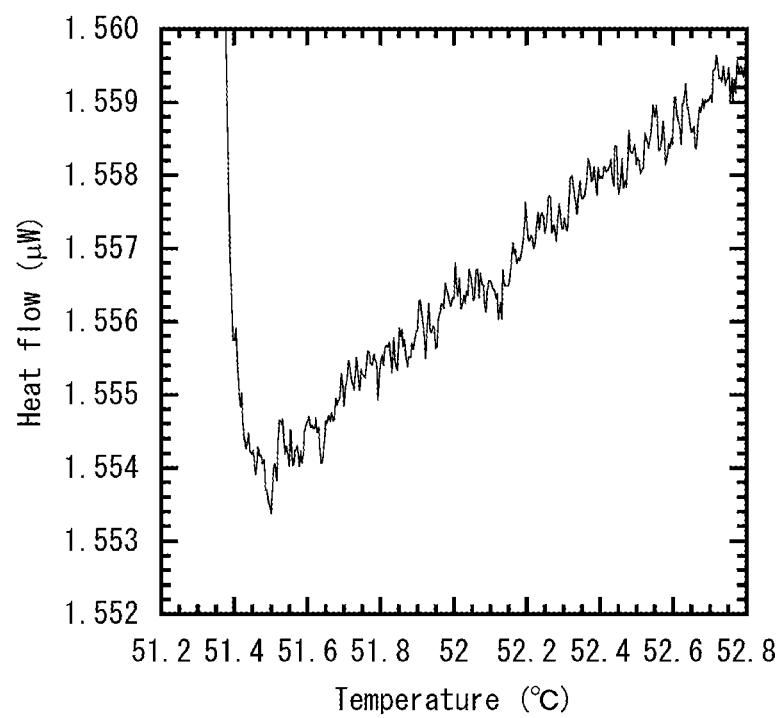

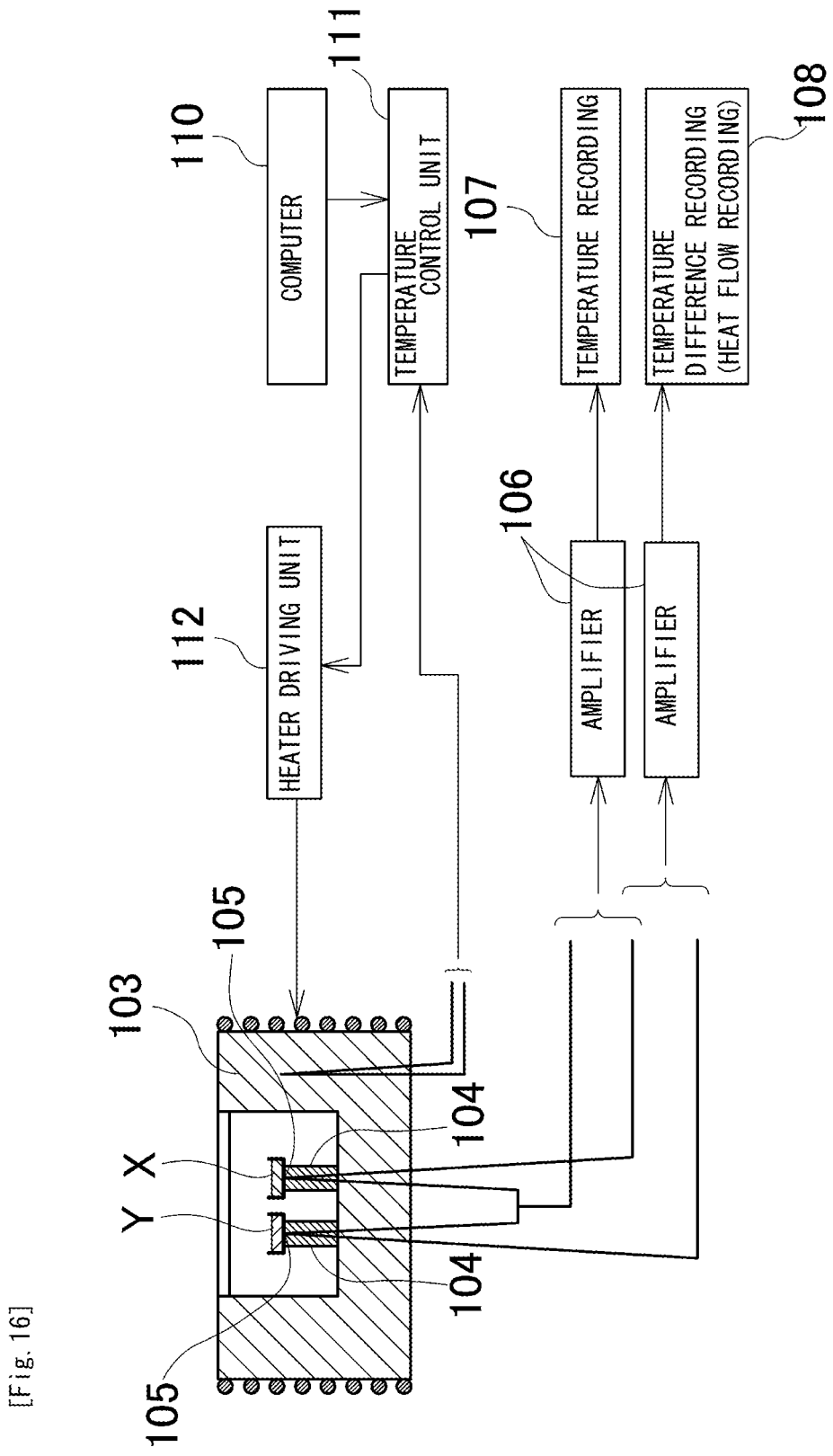
[Fig. 16]

[Fig. 17]
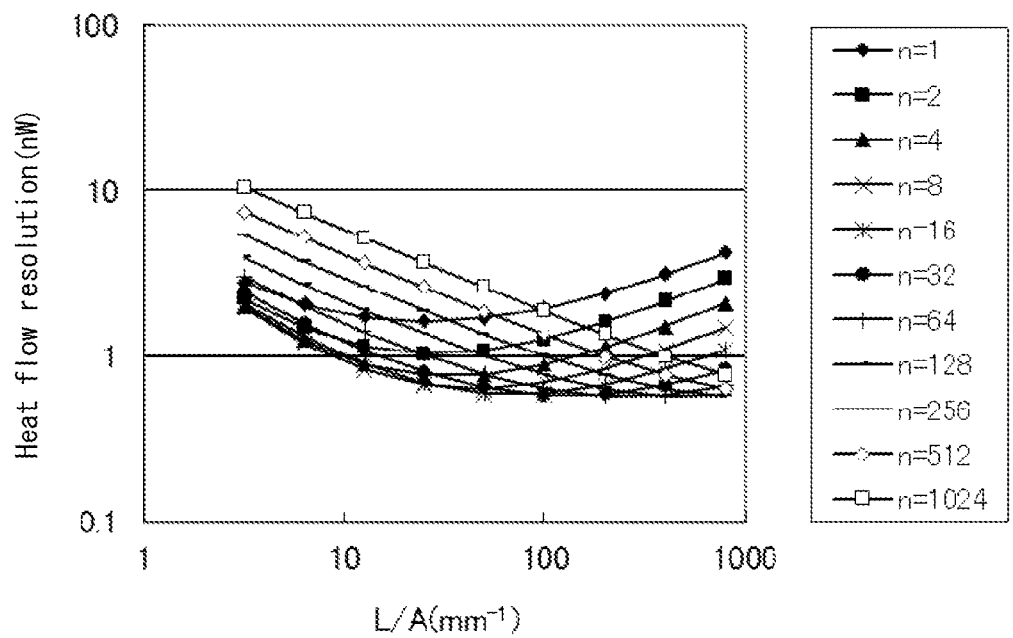
[Fig. 18]
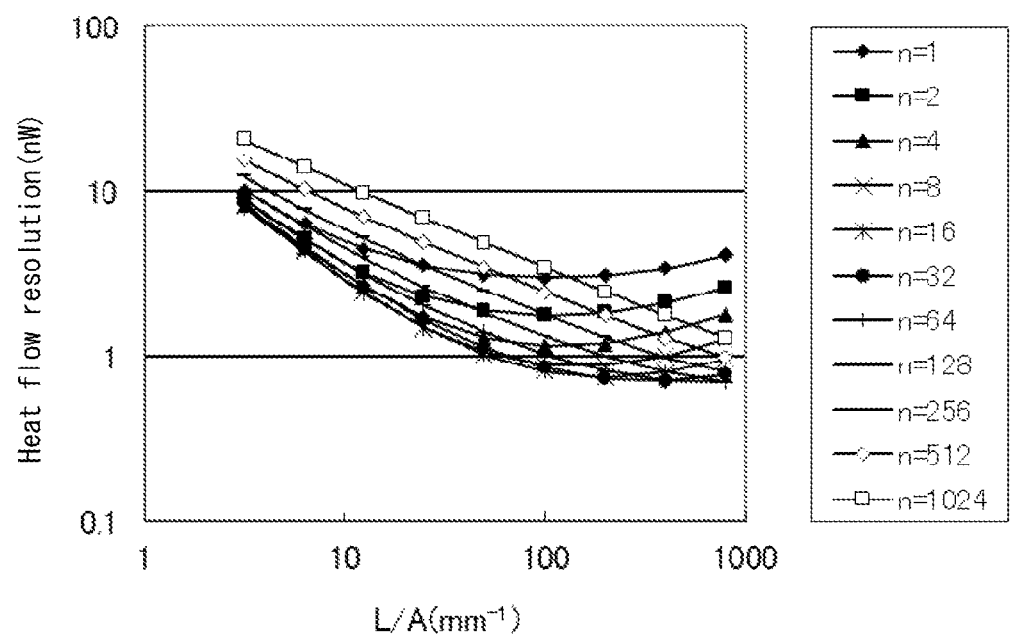

[Fig. 19]
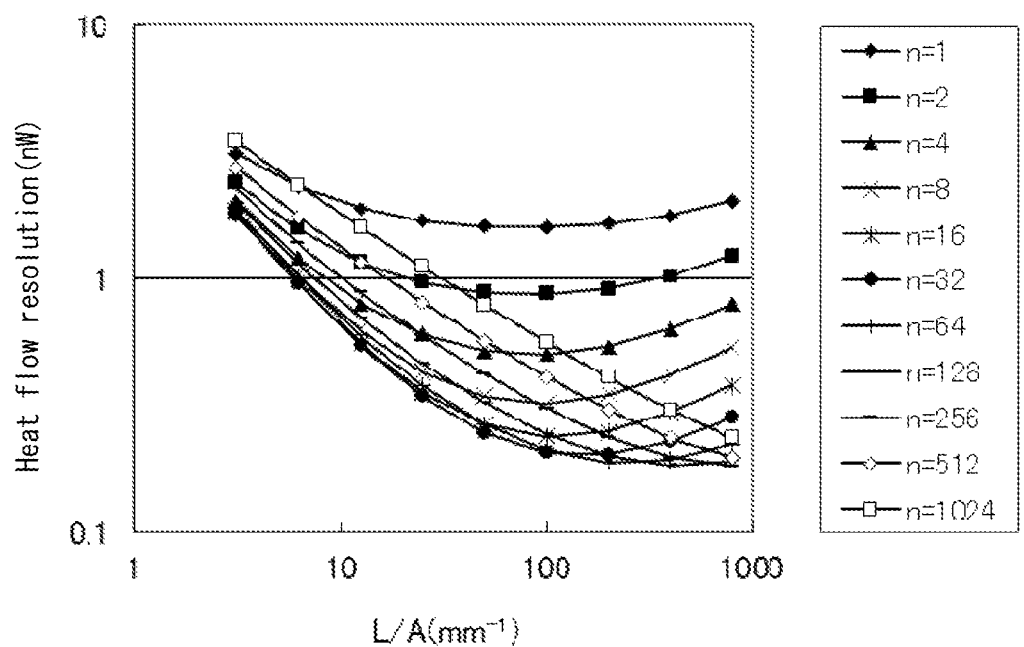
[Fig. 20]
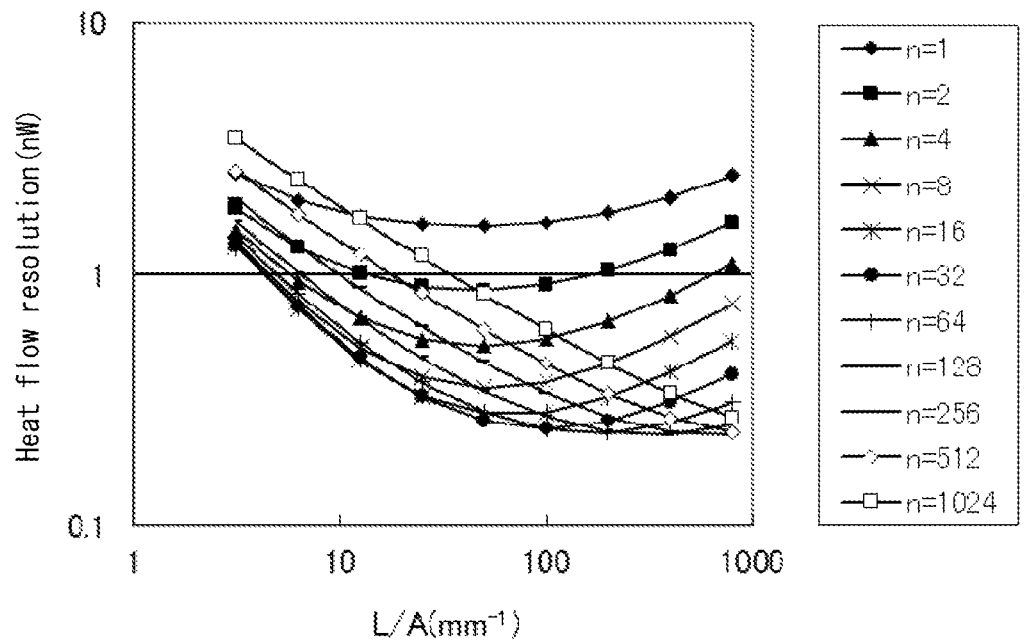

[Fig. 21]
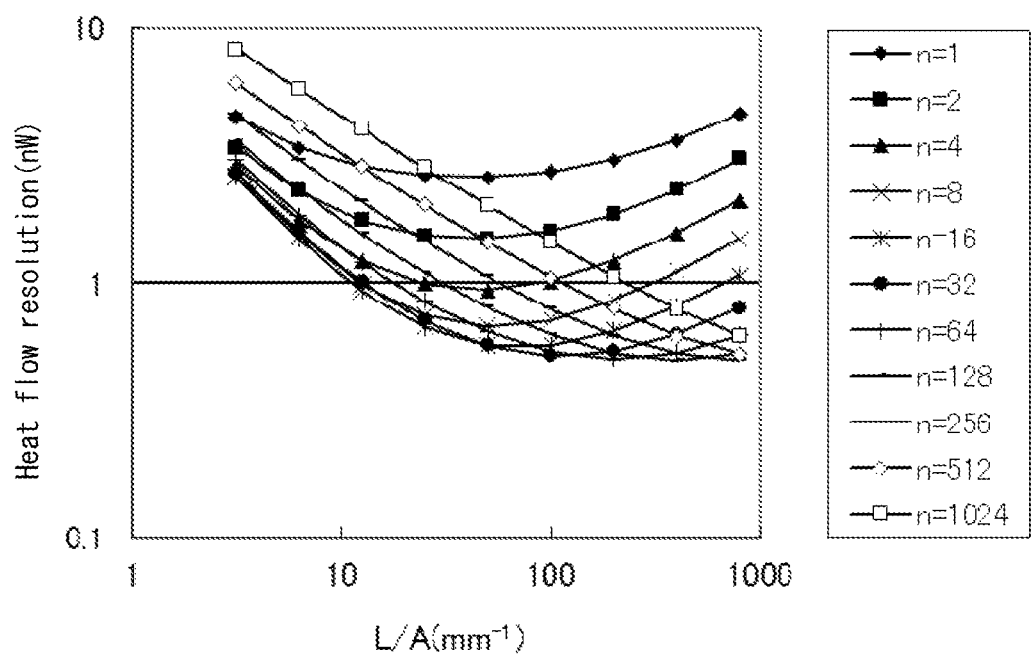

[Fig. 22]
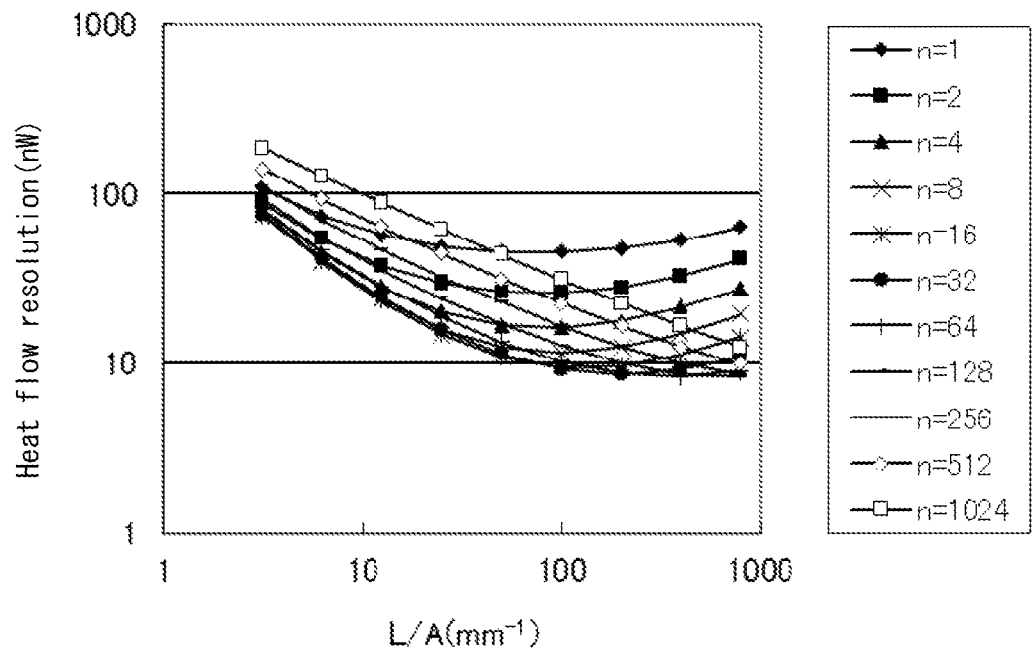
| $T_M$ (K) | 273 |
|---|---|
| $\rho_P, \rho_N$ ($\mu\Omega$m) | 10.2 |
| $\kappa_P, \kappa_N$ (W m$^{-1}$K$^{-1}$) | 1.35 |
| S (mV/K) | 0.007 |
| $K_A$ (W/K) | $5 \times 10^{-4}$ |
| $R_A$ ($\Omega$) | 20 |
| $\Delta f$ (Hz) | 1 |
| $R_W$ ($\Omega$) | 0.15 |

[Fig. 23]
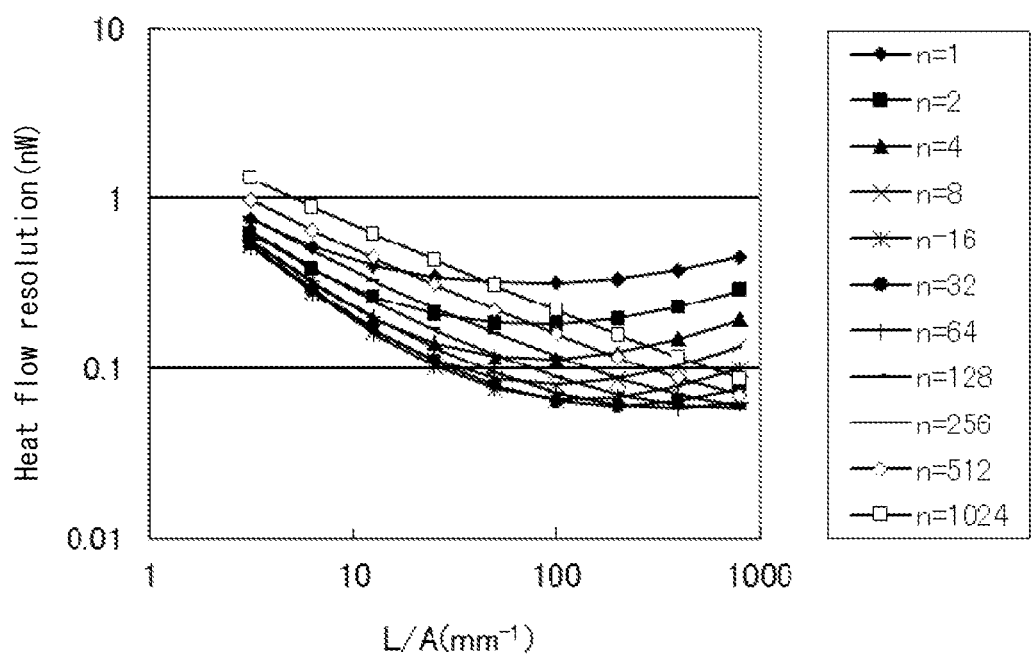
| $T_M$ (K) | 273 |
|---|---|
| $\rho_P, \rho_N$ ($\mu\Omega$m) | 10.2 |
| $\kappa_P, \kappa_N$ (W m$^{-1}$K$^{-1}$) | 1.35 |
| S (mV/K) | 1 |
| $K_A$ (W/K) | $5 \times 10^{-4}$ |
| $R_A$ ($\Omega$) | 20 |
| $\Delta f$ (Hz) | 1 |
| $R_W$ ($\Omega$) | 0.15 |

[Fig. 24]
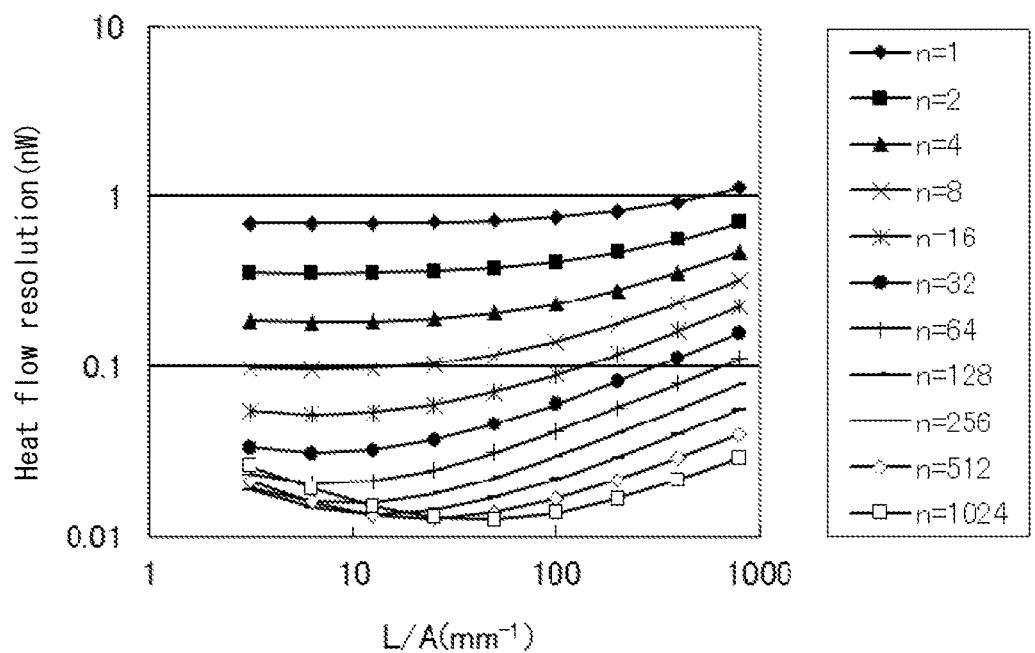
| $T_M$ (K) | 273 |
|---|---|
| $\rho_P, \rho_N$ ($\mu\Omega$m) | 10.2 |
| $\kappa_P, \kappa_N$ (W m$^{-1}$K$^{-1}$) | 0.01 |
| S (mV/K) | 0.4 |
| $K_A$ (W/K) | $5 \times 10^{-4}$ |
| $R_A$ ($\Omega$) | 20 |
| $\Delta f$ (Hz) | 1 |
| $R_W$ ($\Omega$) | 0.15 |

[Fig. 25]
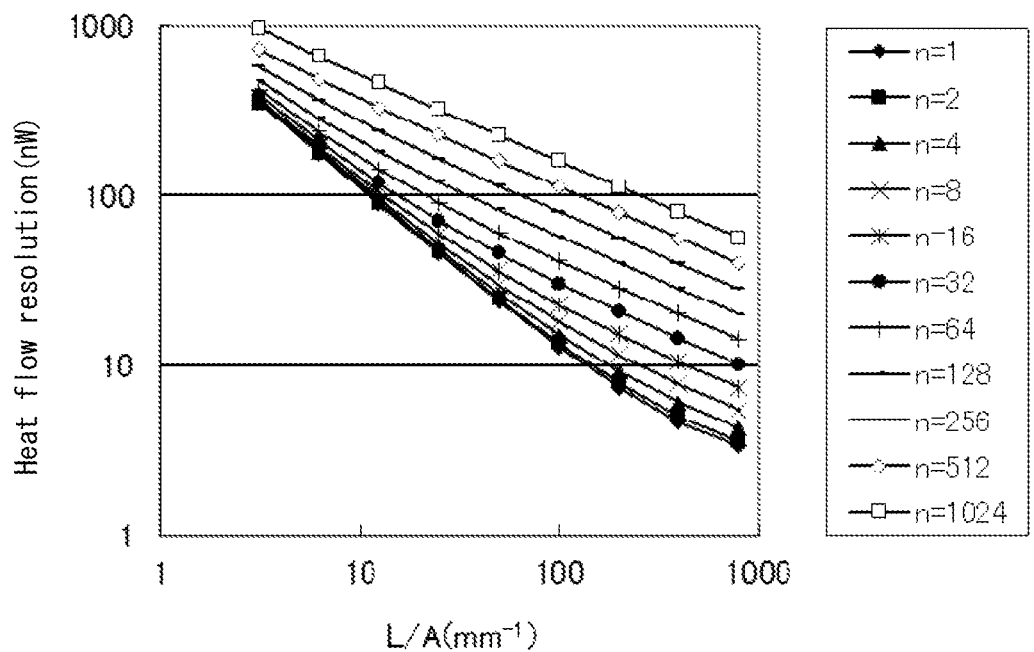
| $T_M$ (K) | 273 |
| --- | --- |
| $\rho_P, \rho_N$ ($\mu \Omega$m) | 10.2 |
| $\kappa_P, \kappa_N$ (W m$^{-1}$K$^{-1}$) | 400 |
| S (mV/K) | 0.4 |
| $K_A$ (W/K) | $5 \times 10^{-4}$ |
| $R_A$ ($\Omega$) | 20 |
| $\Delta f$ (Hz) | 1 |
| $R_W$ ($\Omega$) | 0.15 |

[Fig. 26]
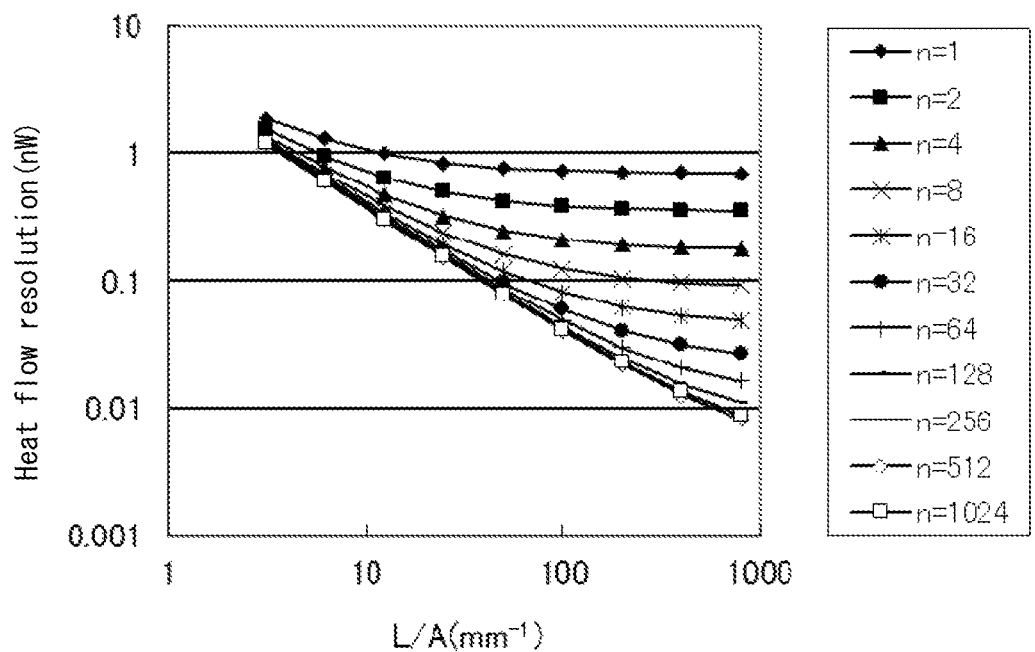
| $T_M$ (K) | 273 |
| --- | --- |
| $\rho_P, \rho_N$ ($\mu\Omega$m) | 0.01 |
| $\kappa_P, \kappa_N$ (W m$^{-1}$K$^{-1}$) | 1.35 |
| S (mV/K) | 0.4 |
| $K_A$ (W/K) | $5 \times 10^{-4}$ |
| $R_A$ ($\Omega$) | 20 |
| $\Delta f$ (Hz) | 1 |
| $R_W$ ($\Omega$) | 0.15 |

[Fig. 27]
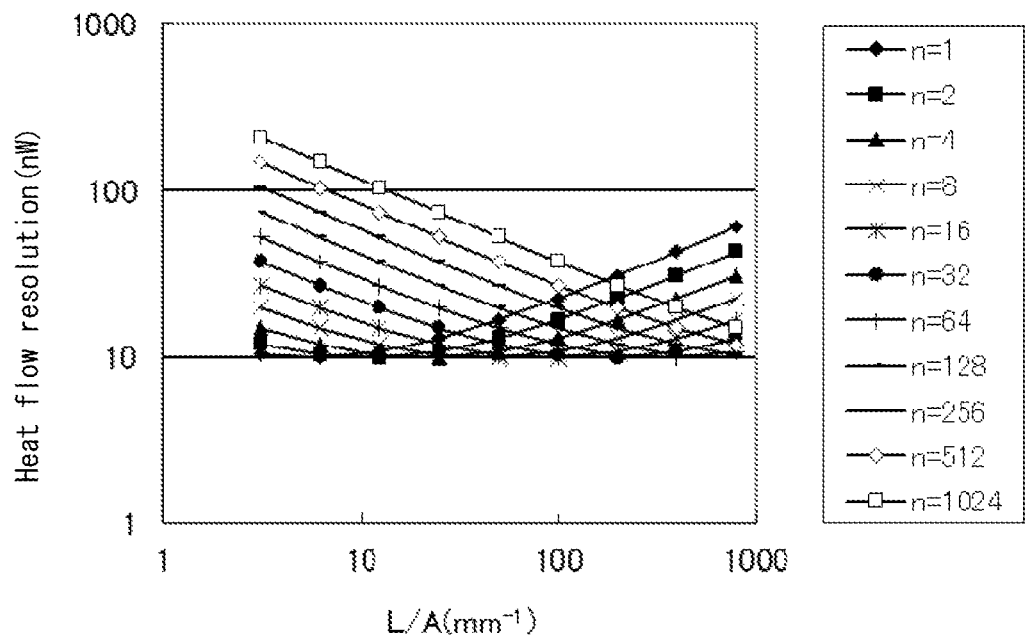
| $T_M$ (K) | 273 |
|---|---|
| $\rho_P, \rho_N$ ($\mu\Omega$m) | 48000 |
| $\kappa_P, \kappa_N$ (W m$^{-1}$K$^{-1}$) | 1.35 |
| S (mV/K) | 0.4 |
| $K_A$ (W/K) | $5\times10^{-4}$ |
| $R_A$ ($\Omega$) | 20 |
| $\Delta f$ (Hz) | 1 |
| $R_W$ ($\Omega$) | 0.15 |

[Fig. 28]
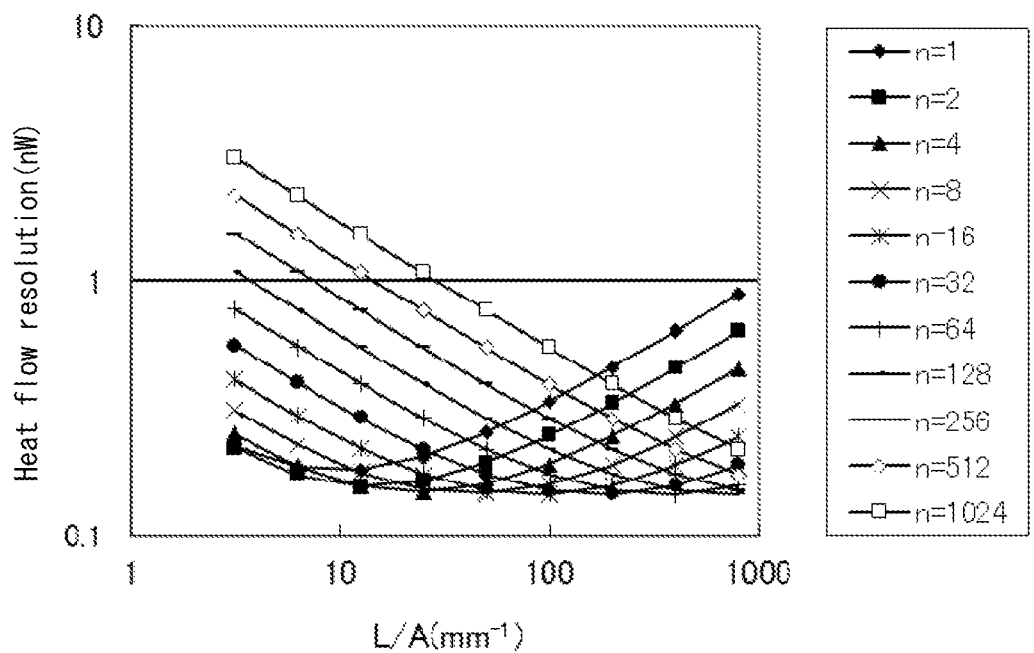
| $T_M$ (K) | 273 |
|---|---|
| $\rho_P, \rho_N$ ($\mu\Omega$m) | 10.2 |
| $\kappa_P, \kappa_N$ (W m$^{-1}$K$^{-1}$) | 1.35 |
| S (mV/K) | 0.4 |
| $K_A$ (W/K) | $5 \times 10^{-4}$ |
| $R_A$ ($\Omega$) | 0.01 |
| $\Delta f$ (Hz) | 1 |
| $R_W$ ($\Omega$) | 0.15 |

[Fig. 29]
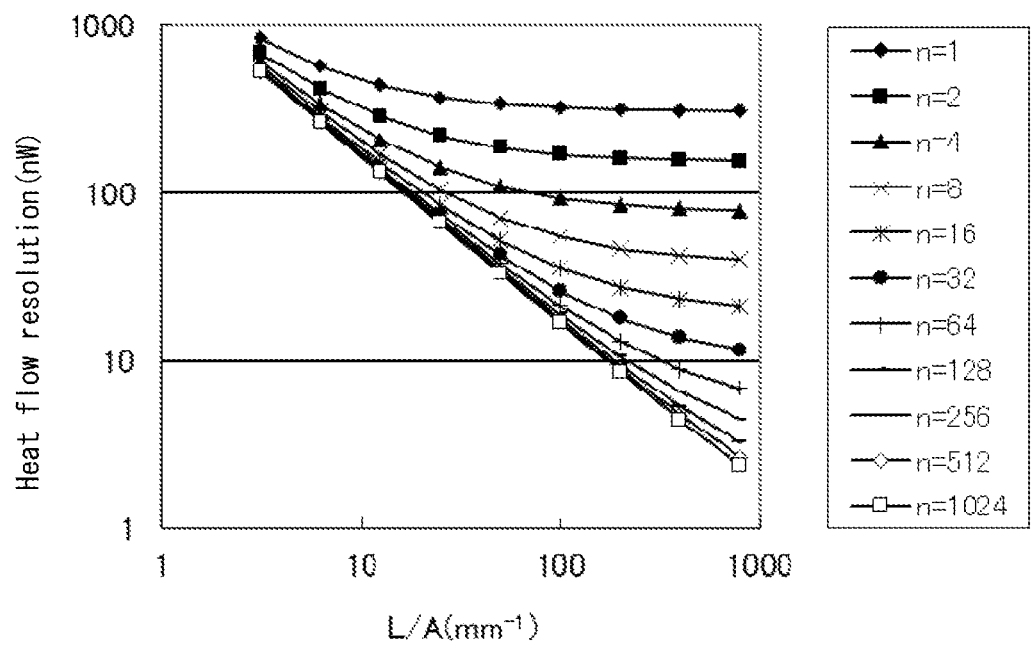
| $T_M$ (K) | 273 |
|---|---|
| $\rho_P, \rho_N$ ($\mu\Omega$m) | 10.2 |
| $\kappa_P, \kappa_N$ (W m$^{-1}$K$^{-1}$) | 1.35 |
| S (mV/K) | 0.4 |
| $K_A$ (W/K) | $5 \times 10^{-4}$ |
| $R_A$ ($\Omega$) | $4 \times 10^6$ |
| $\Delta f$ (Hz) | 1 |
| $R_W$ ($\Omega$) | 0.15 |

[Fig. 30]
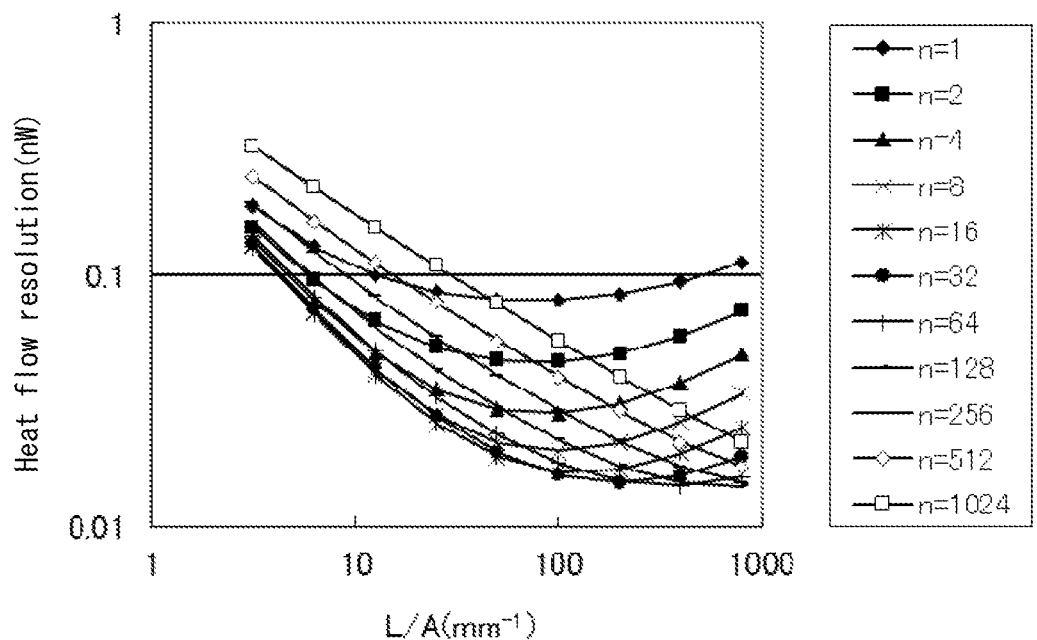
| $T_M$ (K) | 273 |
| --- | --- |
| $\rho_P, \rho_N$ ($\mu\Omega$m) | 10.2 |
| $\kappa_P, \kappa_N$ (W m$^{-1}$K$^{-1}$) | 1.35 |
| S (mV/K) | 0.4 |
| $K_A$ (W/K) | $5 \times 10^{-4}$ |
| $R_A$ ($\Omega$) | 20 |
| $\Delta f$ (Hz) | 0.01 |
| $R_W$ ($\Omega$) | 0.15 |

[Fig. 31]
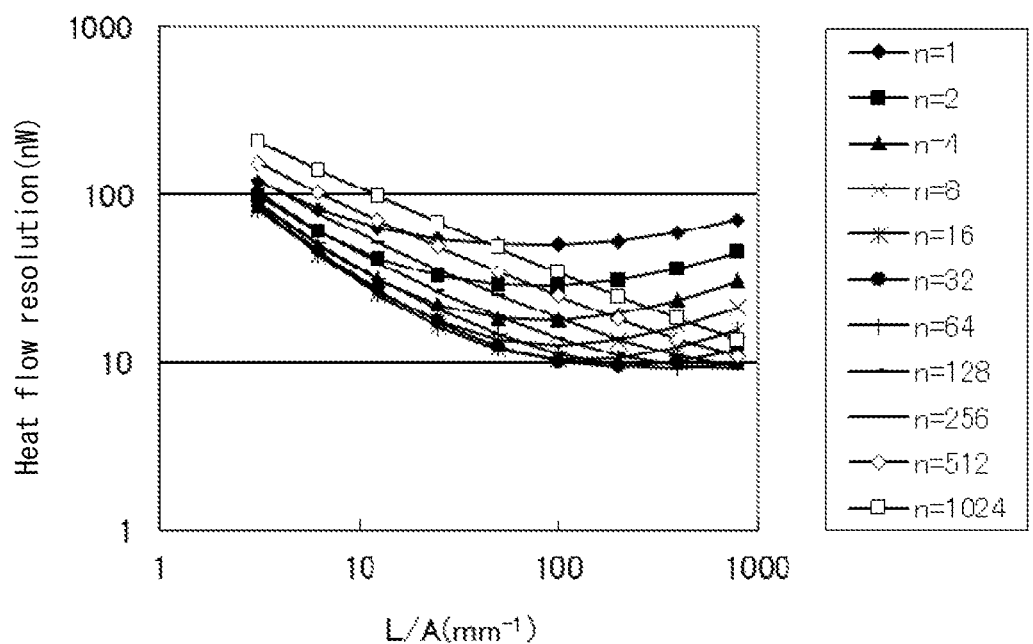
| $T_M$ (K) | 273 |
|---|---|
| $\rho_P, \rho_N$ ($\mu\Omega$m) | 10.2 |
| $\kappa_P, \kappa_N$ (W m$^{-1}$K$^{-1}$) | 1.35 |
| S (mV/K) | 0.4 |
| $K_A$ (W/K) | $5 \times 10^{-4}$ |
| $R_A$ ($\Omega$) | 20 |
| $\Delta f$ (Hz) | 4000 |
| $R_W$ ($\Omega$) | 0.15 |

[Fig. 32]
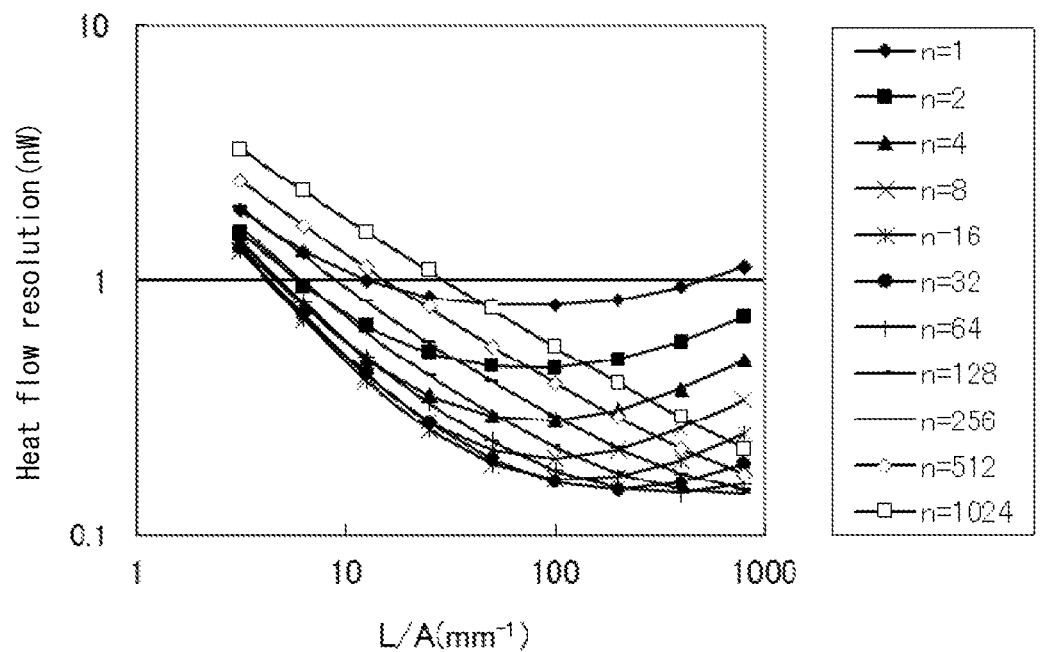
| $T_M$ (K) | 273 |
|---|---|
| $\rho_P, \rho_N$ ($\mu\Omega m$) | 10.2 |
| $\kappa_P, \kappa_N$ (W m$^{-1}$K$^{-1}$) | 1.35 |
| S (mV/K) | 0.4 |
| $K_A$ (W/K) | $5 \times 10^{-4}$ |
| $R_A$ ($\Omega$) | 20 |
| $\Delta f$ (Hz) | 1 |
| $R_W$ ($\Omega$) | 0.01 |

[Fig. 33]
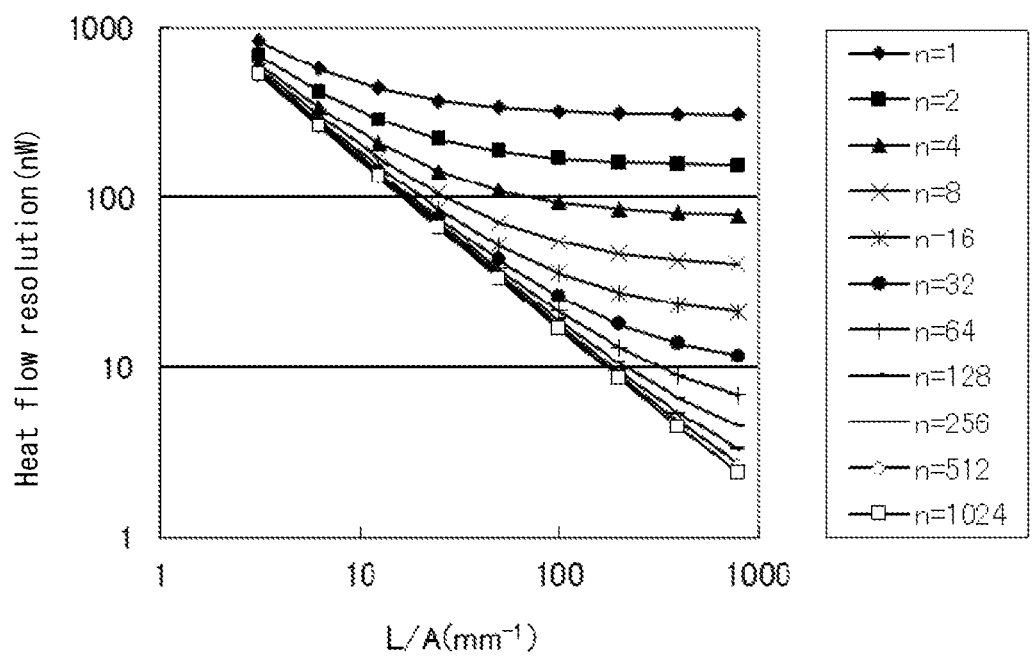
| $T_M$ (K) | 273 |
|---|---|
| $\rho_P, \rho_N$ ($\mu\Omega$m) | 10.2 |
| $\kappa_P, \kappa_N$ (W m$^{-1}$K$^{-1}$) | 1.35 |
| S (mV/K) | 0.4 |
| $K_A$ (W/K) | $5 \times 10^{-4}$ |
| $R_A$ ($\Omega$) | 20 |
| $\Delta f$ (Hz) | 1 |
| $R_W$ ($\Omega$) | $4 \times 10^6$ |

[Fig. 34]
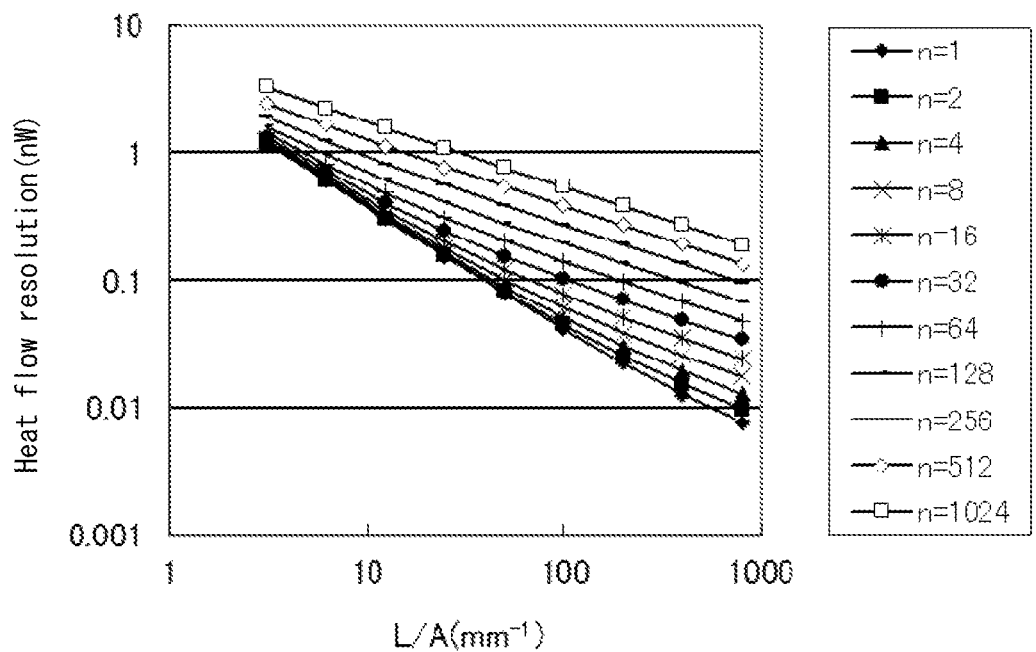
| $T_M$ (K) | 273 |
| --- | --- |
| $\rho_P, \rho_N$ ($\mu\Omega$m) | 10.2 |
| $\kappa_P, \kappa_N$ (W m$^{-1}$K$^{-1}$) | 1.35 |
| S (mV/K) | 0.4 |
| $K_A$ (W/K) | $1 \times 10^{-8}$ |
| $R_A$ ($\Omega$) | 20 |
| $\Delta f$ (Hz) | 1 |
| $R_W$ ($\Omega$) | 0.15 |

[Fig. 35]
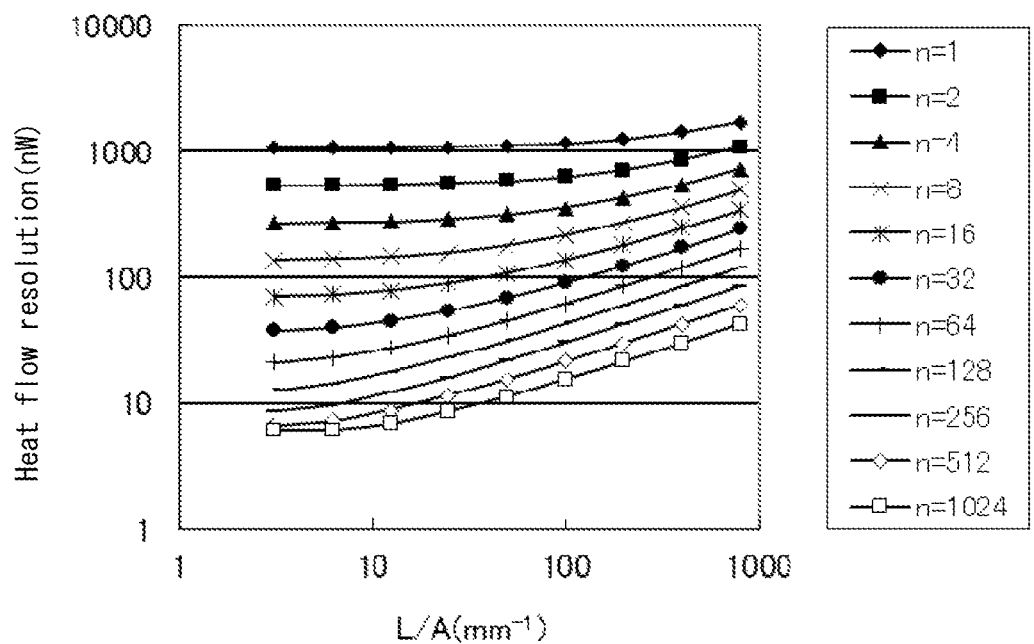
| $T_M$ (K) | 273 |
| $\rho_P, \rho_N$ ($\mu\Omega$m) | 10.2 |
| $\kappa_P, \kappa_N$ (W m$^{-1}$K$^{-1}$) | 1.35 |
| S (mV/K) | 0.4 |
| $K_A$ (W/K) | 0.77 |
| $R_A$ ($\Omega$) | 20 |
| $\Delta f$ (Hz) | 1 |
| $R_W$ ($\Omega$) | 0.15 |

[Fig. 36]
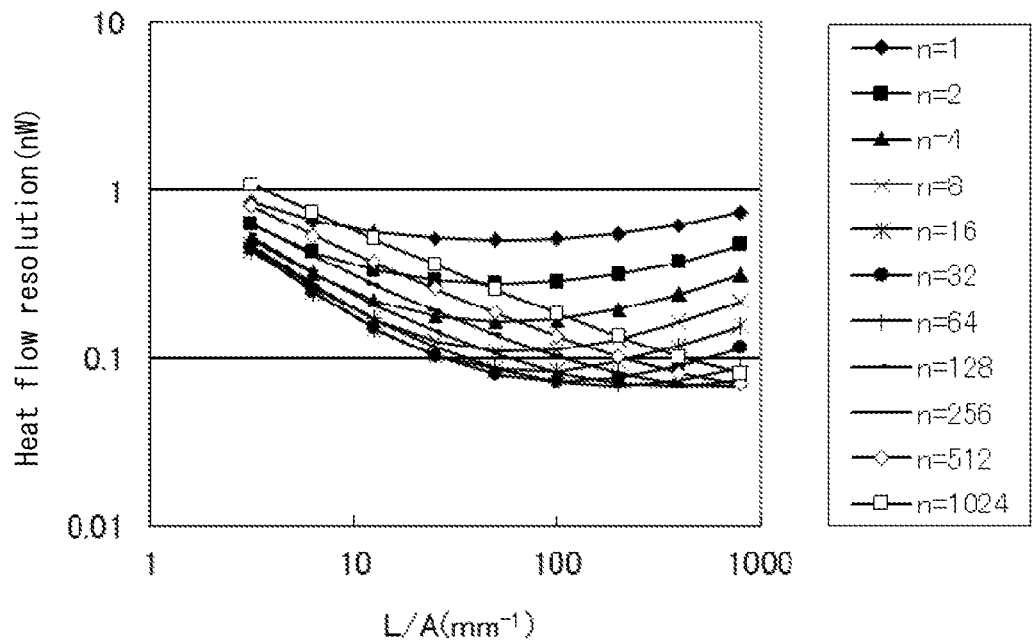

[Fig. 37]
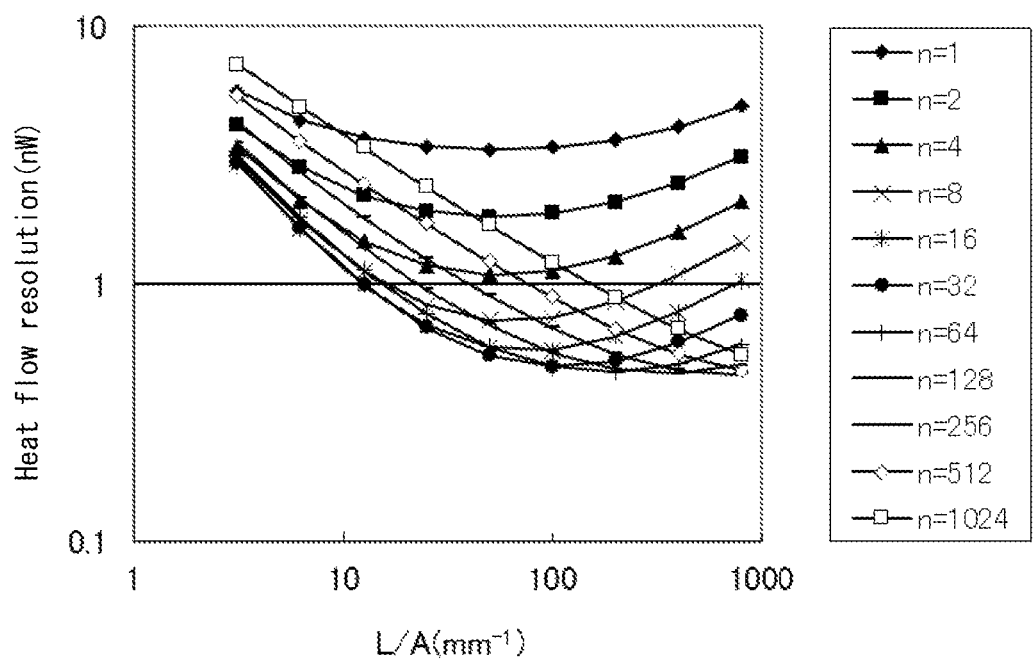
| $T_M$ (K) | 1300 |
|---|---|
| $\rho_P, \rho_N$ ($\mu \Omega$m) | 10.2 |
| $\kappa_P, \kappa_N$ (W m$^{-1}$K$^{-1}$) | 1.35 |
| S (mV/K) | 0.4 |
| $K_A$ (W/K) | $5 \times 10^{-4}$ |
| $R_A$ ($\Omega$) | 20 |
| $\Delta f$ (Hz) | 1 |
| $R_W$ ($\Omega$) | 0.15 |

CALORIMETER AND METHOD FOR DESIGNING CALORIMETER

TECHNICAL FIELD

The present invention relates to a calorimeter and a method for designing the calorimeter that is suitable to remarkably enhance a heat flow resolution when measuring the quantity of heat of a sample.

BACKGROUND ART

Heat release and absorption are always associated with a state change of a substance and thus thermal analysis with calorimeter is applicable to a variety of phenomena including phase transition, such as melting and crystallization, as well as glass transition, heat curing, purity and compatibility and is widely generalized as a method of analysis of organic materials such as polymers and liquid crystals, inorganic materials, such as metal, glass and ceramics, medicals, foods, perfumery, cosmetics or the like. A typical calorimeter employed in thermal analysis is a differential scanning calorimeter (DSC).

The differential scanning calorimeter (DSC) is a device for, while scanning temperature, measuring a difference in heat release and absorption of a sample and a reference substance, and measuring an endothermic and exothermic value due to a state change of a sample. There are two types of DSC, heat flux DSC and power compensation DSC. The heat flux DSC is a method for, while scanning temperature, recording a temperature difference between a sample and a reference substance with respect to time (or temperature). The power compensation DSC is a method for, while scanning temperature, supplying a heat flow to a sample and a reference substance so as to eliminate a temperature difference between a sample and a reference substance, and recording a difference of the supplied heat flow.

FIG. 16 shows a device configuration of a heat flux DSC which is currently widely utilized. This device has a temperature-controlled thermal bath 103, and at a symmetrical position in the thermal bath, a sample X and a reference substance Y are set. Between the thermal bath 103 and the sample X and between the thermal bath 103 and the reference substance Y, thermal resistance bodies 104 are provided, and in predetermined locations of the thermal resistance bodies 104, a temperature difference is detected. Heat release and absorption of the sample X and the reference substance Y is carried out via the thermal resistance bodies 104. A temperature of the thermal bath 103 is managed by a temperature control unit 111, which has received a command from a computer 110, controlling a heater drive unit 112. A difference of a heat flow which is flowing between the thermal bath 103 and the sample X and between the thermal bath 103 and the reference substance Y is in proportion to a temperature difference under detection. This temperature difference is detected by temperature detectors 105 employing temperature-voltage conversion elements (such as thermocouples or thermopiles), the detected difference is output as a thermoelectromotive force difference (DSC signal), and the output difference is input to a temperature recording unit 107 or a temperature difference recording unit 108 via an amplifier 106. The DSC signal is calibrated while a standard substance such as a sapphire of which a heat capacity is known is employed as the sample X, a device constant (V/W) indicative of what V of thermoelectromotive-force difference occurs with respect to a heat flow difference of 1 W is obtained, and the thus obtained constant is converted to a heat flow (W). This device constant is also referred to as calorimetric sensitivity, and in the present specification, it is referred to as calorimetric sensitivity. By time-integrating the DSC signal that is thus converted to the heat flow, the quantity of heat (J) which is released or absorbed is obtained.

A thermal resistance body 104 and a temperature detector 105 are integrated with each other, and are referred to as a heat flux sensor or a heat flow sensor. A heat flux ($W/m^2=J/s \cdot m^2$) is the quantity of heat flowing per unit time per unit area, a heat flow ($W=J/s$) is the quantity of heat flowing per unit time and thus these two elements are different from each other in physical quantities. What is actually measured is a heat flow and thus in the present specification, it is referred to as a heat flow sensor.

Although a general configuration and principles of a differential scanning calorimeter have been described hereinabove, in the field of such differential scanning calorimeter, publicly known techniques shown in Patent Literature 1 and Patent Literature 2 are known as using a semiconductor thermoelectric element or a thermoelectric module (also referred to as Peltier element or thermo-module) as a heat flow sensor instead of a thermoelectric couple so as to thereby have a high sensitivity. Also, as a thermoelectric element, there is a publicly known technique or the like shown in Patent Literature 3.

CITATION LIST

Patent Literature

Patent Literature 1: Japanese Unexamined Patent Application Publication No. 50-66282
Patent Literature 2: Japanese Unexamined Patent Application Publication No. 2004-20509
Patent Literature 3: JP WO2006/043514 Publication

SUMMARY OF THE INVENTION

Problems to be Solved by the Invention

In recent years, in studies of biotechnological fields such as thermodynamic stability of protein and in a variety of research fields and industrial fields of polymers and pharmaceuticals or the like, there has been an increasingly keen desire for a calorimeter which is capable of measuring a further high sensitivity than that of a conventional calorimeter, extremely small heat flow of the order of 10 nW (nano-watts) or less, for example.

In view of such a circumstance, in so far as the one of Patent Literature 1 is concerned, there is a construction is which: one ends of N-type semiconductor thermoelectric elements are respectively secured to a sample container and a reference substance container, the other ends of these semiconductor thermoelectric elements are secured to a metal plate; a difference in thermoelectromotive force of the two semiconductor elements is measured; and a temperature difference of the two sample containers is detected, whereby an thermoelectromotive force of 160 μV/K is obtained; and however, this Literature merely discloses a principal construction of a differential scanning calorimeter, and it is difficult to say that the above calorimeter pursues measurement of extremely small heat flow of the order of 10 nW.

Also, in so far as the one of Patent Literature 2 is concerned, there is proposed a calorimeter in which: as a first measure for enhancing resolution of a heat flow, temperature control is multi-stepped to improve a heating/ cooling control method; as a second measure, a thermal distance between a heat flux sensor and a thermo module is optimized; as a third measure, a semiconductor thermoelectric element is employed in a heat flux sensor and a difference in thermoelectromotive force between a first semiconductor thermoelectric element and a second thermoelectric element is detected, and further, through these three measures, heat flow up to the order of ±5, namely 10 nW can be measured. However, there is no conceptual idea to optimize the semiconductor thermoelectric elements themselves and a calorimeter having a resolution of 10 nW or less has not been substantiated.

On the other hand, in so far as to the one of Patent Literature 3 is concerned, there is proposed a high function type Peltier/Seebeck element and a method for manufacturing the same element, such that, in order to lessen thermal conduction from one ends to the other ends of a first conductive member and a second conductive member having their different Seebeck coefficients, a cross-sectional area of an intermediate portion in a respective one of lengthwise directions is made so as to be smaller than a cross-sectional area of each end portion thereof, whereby thermal conductivity of the intermediate portion is set to be smaller than thermal conductivity of each end portion; or alternatively, instead of setting the cross-sectional area to be smaller, the intermediate portions of the conductive members are divided into a plurality to vary sectional shapes or a material for the intermediate portions is formed by employing amorphous silicon or the like with its smaller thermal conductivity than a material for each end portion, whereby a temperature difference between a heating side of the Peltier/Seebeck element and an opposite side thereto can be maintained as a predetermined temperature difference for a long time.

Although it is considered that this Seebeck element is employed in a calorimeter, if a thermal resistance of an intermediate portion is increased, an electric resistance also increases and thus only a smaller current than that of a thermoelectric element which does not form an intermediate portion can be flowed, which is identical to employing a thermoelectric element of a small maximum current value which forms an intermediate portion. Also, if the intermediate portion is formed, the element becomes mechanically weak, and its structure becomes complicated and thus manufacturing thereof is difficult. In addition, it is difficult to say that the prior art aims at optimization of a shape or a structure of the thermoelectric element for the sake of measurement of a minute heat flow.

In outlining a current differential scanning calorimeter, the constituent elements or shapes are generalized, and in such generalized specification, the limit is measurement of a heat flow resolution up to 100 nW at most. As such a cause, it is considered that the calorimetric sensitivity of a heat flow sensor is low.

In a case where an attempt is made to keep track of a minute heat anomaly of protein or the like, for example, by employing such calorimeter of low resolution, it is not impossible to increase a temperature scanning rate and then increase a DSC signal. However, if the scanning rate is increased, a temperature resolution lowers, and the temperature or the shape of heat anomaly varies and thus as a result, analysis with high precision cannot be carried out.

In a differential scanning calorimeter employing a thermoelectric module as a heat flow sensor as well, although a signal voltage can be obtained as a larger value than that of a device employing a thermopile, as a current calorimeter, a commercially available thermoelectric module designed for thermoelectric cooling, including its shape, size or the like, there is no conceptual idea to optimize the module for the sake of measurement of a heat flow, and the heat flow resolution still remains on the order of 10 to 50 nV or more and thus it is difficult to say that the performance is fully pursued to an extent such that precise analysis can be carried out.

Accordingly, it is an object of the present invention to achieve optimization of a thermoelectric module in order to pursue a performance of the thermoelectric module as a heat flow sensor. As a result of further studies, although it is generally considered that a calorimetric sensitivity increases with increasing the number n of pairs of thermoelectric elements, it was newly found that: the calorimetric sensitivity does not vary when a thermal conductance $K_M$ of the thermoelectric module is sufficiently larger than a thermal conductance $K_A$ due to constituent elements other than the thermoelectric elements, gas or the like; the calorimetric sensitivity saturates if, in order to enhance the calorimetric sensitivity, a ratio L/A of the length L and area A of the thermoelectric element is increased and then the thermal conductance $K_M$ is made smaller than the thermal conductance $K_A$; a heat flow resolution lowers if the L/A ratio is too large; and the thermal conductance $K_A$ varies depending on convection or the like and thus it is better that the thermal conductance $K_M$ is larger than the thermal conductance $K_A$.

According to the foregoing description, it is an object of the present invention to study a condition of a thermoelectric module suitable for calorimeter in order to further enhance the resolution of a calorimeter, and provide a calorimeter having a resolution of a heat flow of 10 nW or less including a differential scanning calorimeter and a calorimeter designing method suitable for realization thereof.

Means for Solving the Problem

In order to achieve such an object, the present invention employs the following means.

That is, a calorimeter according to the first invention is directed to a calorimeter in which a sample is provided so that heat flows in and out of the sample via a thermoelectric module in a temperature-controlled thermal bath, and a voltage is taken out according to the heat flow going in and out of the sample at a time of endothermic or exothermic process, at a predetermined position of the thermoelectric module, wherein the thermoelectric module is so configured that a pair of a P-type thermoelectric element and an N-type thermoelectric element is disposed between substrates, and the pair of the P-type thermoelectric element and the N-type thermoelectric element are connected in n pairs so that the P-type thermoelectric element and the N-type thermoelectric element are arranged alternately in π-shape;

the calorimeter is configured to take out a thermoelectromotive force which includes a noise based on an electric resistance of the thermoelectric module and is generate at the thermoelectric module by the heat flow going in and out of the sample, and amplify the thermoelectromotive force with a ultralow noise amplifier connected to the thermoelectric module through lead wires; and an L/A ratio (L: length and A: cross-sectional area) of the thermoelectric element constituting the thermoelectric module and the number n of the pairs of the thermoelectric elements are set so that: the L/A ratio is 6 mm$^{-1}$ or more; the number n of the pairs is in a range of 4 or more; and a relationship between a thermal conductance $K_M$ between the substrates constituting the thermoelectric module which depends on the L/A ratio and the number n of the pairs, and a thermal conductance $K_A$ due to conduction, convection, and thermal radiation depending on a correlation of the thermal bath and the thermoelectric module, is $K_M \geq K_A$.

By setting the L/A ratio and the number n of the pairs according to such configuration, a heat flow resolution represented by the calorimetric sensitivity and a noise of the thermoelectric module can be remarkably improved in comparison with that of the prior art.

In addition, a calorimeter according to the second invention is directed to a calorimeter in which a sample is provided so that heat flows in and out of the sample via a thermoelectric module in a temperature-controlled thermal bath, and a voltage is taken out according to the heat flow going in and out of the sample at a time of endothermic or exothermic process, at a predetermined position of the thermoelectric module, wherein:

the thermoelectric module is so configured that a pair of a P-type thermoelectric element and an N-type thermoelectric element is disposed between substrates, and the pair of the P-type thermoelectric element and the N-type thermoelectric element are connected in n pairs so that the P-type thermoelectric element and the N-type thermoelectric element are arranged alternately in π-shape, the calorimeter is configured to take out a thermoelectromotive force which includes a noise based on an electric resistance of the thermoelectric module and is generated at the thermoelectric module by the heat flow going in and out of the sample, and amplify the thermoelectromotive force with a ultralow noise amplifier connected to the thermoelectric module through lead wires; and an L/A ratio (L: length and A: cross-sectional area) of the thermoelectric element constituting the thermoelectric module and the number n of the pairs of the thermoelectric elements are set so that: the L/A ratio is 6 mm$^{-1}$ or more; the number n of the pairs is in a range of 4 or more; and a relationship of $xR_M \geq R_A - R_W$ is established among an electric resistance $R_M$ of the thermoelectric module, the number x of the thermoelectric modules, an equivalent noise resistance $R_A$ of the ultralow noise amplifier, and a resistance $R_W$ of the lead wire.

By setting the L/A ratio and the number n of the pairs according to such configuration, a heat flow resolution represented by the calorimetric sensitivity and a noise of the thermoelectric module can be also remarkably improved in comparison with that of the prior art.

Alternatively, in order to carry out an appropriate design considering strength or the like of a thermoelectric module without degrading a heat flow resolution, it is preferable to select the L/A ratio and the number n of the pairs so that the heat flow resolution is within 50 times to 10 times of a saturation value when the L/A ratio is varied under a predetermined number n of the pairs.

In the foregoing description, it is preferable to select the L/A ratio and the number n of the pairs so that the heat flow resolution (noise/calorimetric sensitivity) is 10 nW or less.

Alternately, it is preferable to select the L/A ratio and the number n of the pairs so that a heat flow resolution (noise/calorimetric sensitivity) is 5 nW or less.

Alternately, it is preferable to select the L/A ratio and the number n of the pairs so that a heat flow resolution (noise/calorimetric sensitivity) is 1 nW or less.

On the other hand, a method for designing a calorimeter according to the present invention, the calorimeter being so constituted that a sample is provided via a thermoelectric module in a temperature-controlled thermal bath and a temperature of the sample is detected at a predetermined position of the thermoelectric module, is characterized by, as shown in FIG. 1, defining a function F of a heat flow resolution (noise/calorimetric sensitivity) while an L/A ratio (L: length and A: cross-sectional area) and the number n of pairs of thermoelectric elements constituting the thermoelectric module are employed as variables; and based on the function, selecting the L/A ratio and the number n of the pairs, the function including respective values of:

a thermal conductance $K_A$ according to at least any of thermal conduction via an atmosphere around the thermoelectric module or a reinforcement member such as a material filled between the thermoelectric elements constituting the thermoelectric module, convection of the atmosphere, and thermal radiation through the atmosphere;

a thermal conductance $K_M$ between substrates of the thermoelectric module; and an electric resistance of the thermoelectric module as a noise parameter.

According to such a method, since the L/A ratio (L: length and A: cross-sectional area) of a semiconductor element and a heat flow resolution can be appropriately associated with each other in consideration of an influence of the thermal conductance $K_A$ or a thermal noise which cannot be ignored in reducing the heat flow resolution of a calorimeter to its limit, it becomes possible to easily and appropriately select the L/A ratio and the number n of the pairs such that a predetermined heat flow resolution can be obtained even in case where a configuration or a shape of the calorimeter varies.

As a specific embodiment, as constituting a calorimeter so that a sample is provided via a thermoelectric module in a temperature-controlled thermal bath and a temperature of the sample is detected at a predetermined position of the thermoelectric module, there is exemplified a method, wherein: an L/A ratio and the number n of the pairs are selected based on:

$$\text{Heat flow resolution (W)} = \frac{\text{Noise(V)}}{\text{Calorimetric sensitivity(V/W)}}$$

$$= \frac{1}{S}\left[\left(\kappa_P \frac{A_P}{L_P} + \kappa_N \frac{A_N}{L_N}\right) + \frac{K_A}{n}\right]\sqrt{4k\Delta f\left(xT_M n\left(\rho_P \frac{L_P}{A_P} + \rho_N \frac{L_N}{A_N}\right) + T_A R_A + T_W R_W\right)}$$

where: x is the number of thermoelectric modules;

$A_P$ is a cross-sectional area of a P-type thermoelectric element;

$L_P$ is a length of the P-type thermoelectric element;

$A_N$ is a cross-sectional area of an N-type thermoelectric element;

$L_N$ is a length of the N-type thermoelectric element;
$\rho_P$ is an electrical resistivity of the P-type thermoelectric element;
$\rho_N$ is an electrical resistivity of the N-type thermoelectric element;
n is the number of the pairs of thermoelectric elements constituting a thermoelectric module;
$R_M$ is an electric resistance of a thermoelectric module;
$T_M$ is an absolute temperature of the thermoelectric module;
$R_W$ is a resistance of lead wires between the thermoelectric module and an amplifier;
$T_W$ is an absolute temperature of the lead wire;
$R_A$ is an equivalent noise resistance of the amplifier;
$T_A$ is a standard noise temperature;
k is the Boltzmann constant;
$\Delta f$ is a frequency bandwidth to be measured;
$\kappa_P$ is a thermal conductivity of a P-type thermoelectric element;
$\kappa_N$ is a thermal conductivity of an N-type thermoelectric element;
S (V/K) is a Seebeck coefficient of a thermoelectric material;
$K_M$ (W/K) is a thermal conductance between substrates of a thermoelectric module (composed of n pairs of thermoelectric elements); and
$K_A$ (W/K) is a thermal conductance due to conduction, convection, and thermal radiation.

In order to suitably carry out such a method, it is effective to employ a designing program which includes a function for computing a heat flow resolution while an L/A ratio (L: length and A: cross-sectional area) and the number n of the pairs of thermoelectric elements of a thermoelectric module are employed as variables, the values of the L/A ratio and the number n of the pairs are assigned to this function, and which is configured to execute computation to thereby compute the heat flow resolution.

By applying the function related to the heat flow resolution as described above and selecting the L/A ratio and the number n of the pairs, it becomes easy to select the L/A ratio and the number n of the pairs so that the heat flow resolution (noise/calorimetric sensitivity) is 10 nW or less, and a calorimeter remarkably enhancing the heat flow resolution in comparison with the prior art can be easily appropriately configured.

Alternately, it also becomes possible to select the L/A ratio and the number of the pairs so that the heat flow resolution (noise/calorimetric sensitivity) is 5 nW or less, and a calorimeter remarkably enhancing the heat flow resolution in comparison with the prior art can be easily appropriately configured.

Furthermore, it also becomes possible to select the L/A ratio and the number of the pairs so that the heat flow resolution (noise/calorimetric sensitivity) is 1 nW or less, and a calorimeter remarkably enhancing the heat flow resolution in comparison with the prior art can be easily appropriately configured.

Incidentally, the above descriptive matters can be applied to part of a thermoelectric module without being always limitative to applying an entire thermoelectric module constituting a calorimeter. In this case, although an advantageous effect of reducing a heat flow resolution decreases, other advantageous effects such as enhancing a mechanical strength and facilitating manufacturing can be attained.

Effects of the Invention

The present invention is directed to the method and configuration described above and thus it becomes possible to appropriately treat thermal conductance due to thermal conduction, convection and thermal radiation of gas or the like, and thermal noise of a thermoelectric module which cannot be ignored when an attempt is made to form a calorimeter with an ultrahigh sensitivity, and remarkably enhance a heat flow resolution of the calorimeter to 10 nW or less, preferably 5 nW, or further preferably 1 nW or less in comparison with the prior art, without employing a complicated structure for the thermoelectric element. In addition, by substantiating such a high performance calorimeter, even if a temperature scanning rate is reduced, a sufficient thermoelectromotive force can be obtained from a thermoelectric module, a minute heat anomaly such as thermal denaturation of protein can be precisely measured, and the calorimeter is applicable to and is effective for use in a variety of measurement objects such as biological samples or stratum corneum, liquid crystals.

BRIEF DESCRIPTION OF THE DRAWINGS

FIG. 1 is a view conceptually showing a method of the present invention.

FIG. 2 is a view showing a differential scanning calorimeter according to one embodiment of the present invention.

FIG. 3 is a view showing a thermoelectric module constituting the same calorimeter as above.

FIG. 4 is a schematic structural view of the same thermoelectric module as above.

FIG. 5 is an explanatory view related to a thermoelectric element constituting the same thermoelectric module as above.

FIG. 6 is an explanatory view related to a thermal conductance of the same thermoelectric module as above.

FIGS. 7 (a) and (b) are views showing a mode of use of the same thermoelectric module as above.

FIG. 8 is a graph depicting dependency of a calorimetric sensitivity relative to an L/A ratio and the number n of pairs in respect of the same thermoelectric module as above.

FIG. 9 is a graph depicting dependency of a noise (V) relative to an L/A ratio and the number n of pairs in respect to the same thermoelectric module as above.

FIGS. 10 (a) and (b) are graphs depicting dependency of a heat flow resolution (W) relative to an L/A ratio and the number n of pairs in respect to the same thermoelectric module as above.

FIG. 11 is a table showing a value of a noise under a predetermined temperature of an ultrahigh sensitivity DSC using a proto-typed thermoelectric module.

FIG. 12 is a table showing a value of a heat flow resolution under the predetermined temperature of the ultrahigh sensitivity DSC using the proto-typed thermoelectric module.

FIG. 13 is a graph illustrating baseline data due to a differential scanning calorimeter according to the present invention.

FIG. 14 is a graph illustrating a noise due to the differential scanning calorimeter according to the present invention.

FIG. 15 is a graph depicting a measurement example due to the differential scanning calorimeter according to the present invention.

FIG. 16 is an entire structural view showing a device configuration of a general heat flux scanning calorimeter (heat flux DSC).

FIG. 17 is a graph depicting dependency of a heat flow resolution (W) relative to an L/A ratio and the number n of pairs when Pb—Te is employed as a thermoelectric material.

FIG. 18 is a graph depicting dependency of the heat flow resolution (W) relative to the L/A ratio and the number n of pairs when Si—Ge is employed as a thermoelectric material.

FIG. 19 is a graph depicting dependency of the heat flow resolution (W) relative to the L/A ratio and the number n of pairs when a $Bi_2Te_3$-based material is employed as a thermoelectric material and a thermal bath temperature is 175K.

FIG. 20 is a graph depicting dependency of the heat flow resolution (W) relative to the L/A ratio and the number n of pairs when the $Bi_2Te_3$-based material is employed as the thermoelectric material and the thermal bath temperature is 338K.

FIG. 21 is a graph depicting dependency of the heat flow resolution (W) relative to the L/A ratio and the number n of pairs when the $Bi_2Te_3$-based material is employed as the thermoelectric material and the thermal bath temperature is 520K.

FIG. 22 is a graph depicting dependency of the heat flow resolution (W) relative to the L/A ratio and the number n of pairs when S is decreased.

FIG. 23 is a graph depicting dependency of the heat flow resolution (W) relative to the L/A ratio and the number n of pairs when S is increased.

FIG. 24 is a graph depicting dependency of the heat flow resolution (W) relative to the L/A ratio and the number n of pairs when $\kappa_P$, $\kappa_N$ are decreased assuming that $\kappa_P=\kappa_N$.

FIG. 25 is a graph depicting dependency of the heat flow resolution (W) relative to the L/A ratio and the number n of pairs when $\kappa_P$, $\kappa_N$ are increased assuming that $\kappa_P=\kappa_N$.

FIG. 26 is a graph depicting dependency of the heat flow resolution (W) relative to the L/A ratio and the number n of pairs when $\rho_P$, $\rho_N$ are decreased assuming that $\rho_P=\rho_N$.

FIG. 27 is a graph depicting dependency of the heat flow resolution (W) relative to the L/A ratio and the number n of pairs when $\rho_P$, $\rho_N$ are increased assuming that $\rho_P=\rho_N$.

FIG. 28 is a graph depicting dependency of the heat flow resolution (W) relative to the L/A ratio and the number n of pairs when $R_A$ is decreased.

FIG. 29 is a graph depicting dependency of the heat flow resolution (W) relative to the L/A ratio and the number n of pairs when $R_A$ is increased.

FIG. 30 is a graph depicting dependency of the heat flow resolution (W) relative to the L/A ratio and the number n of pairs when $\Delta f$ is decreased.

FIG. 31 is a graph depicting dependency of the heat flow resolution (W) relative to the L/A ratio and the number n of pairs when $\Delta f$ is increased.

FIG. 32 is a graph depicting dependency of the heat flow resolution (W) relative to the L/A ratio and the number n of pairs when Rw is decreased.

FIG. 33 is a graph depicting dependency of a heat flow resolution (W) relative to the L/A ratio and the number n of pairs when Rw is increased.

FIG. 34 is a graph depicting dependency of the heat flow resolution (W) relative to the L/A ratio and the number n of pairs when $K_A$ is decreased.

FIG. 35 is a graph depicting dependency of the heat flow resolution (W) relative to the L/A ratio and the number n of pairs when $K_A$ is increased.

FIG. 36 is a graph depicting dependency of the heat flow resolution (W) relative to the L/A ratio and the number n of pairs when $T_M$ is decreased.

FIG. 37 is a graph depicting dependency of the heat flow resolution (W) relative to the L/A ratio and the number n of pairs when $T_M$ is increased.

MODE FOR CARRYING OUT THE INVENTION

Hereinafter, one embodiment of the present invention will be described with reference to the drawings.

FIG. 2 shows that the present invention is applied to a differential scanning calorimeter for detecting a temperature difference between a sample X and a reference substance Y, and in an internal space $S_1$ of an airtight container C, an aluminum-based outside shell 4 is disposed via thermoelectric modules (Peltier element) 5 for temperature regulation. Here, the sample X and the reference substance Y come under the term "sample(s)" that is referred to as in the present invention. At a bottom part of the outside shell 4, a platinum resistance thermometer for temperature regulation 10 is embedded; the thermometer is read by a programmable temperature controller 11; and the controller 11 feedback controls a current to be supplied to thermoelectric modules for temperature regulation 5 so that the bottom part of the outside shell 4 is at a desired temperature through a bipolar power supply 12. In an inside space $S_1$ of the outside shell 4, an aluminum-based inside shell 3 is further disposed via a thermal resistance body 34 with a bottom thereof being at the bottom part of the outside shell 4. The airtight container C is a half-split structure which is vertically openable; the shells 3, 4 are a lidding structure which is vertically openable in the inside spaces $S_2$, $S_3$; and both of these shells close inside spaces $S_1$, $S_2$, $S_3$ at the time of lidding. In addition, in the inside space $S_3$ of the inside shell 3, a copper-based block 21 serving as a thermal bath and a sample holder 2 made of a copper-based lid 22 are disposed via a thermal resistance body 23 with a bottom part thereof being the bottom part of the inside shell 3. The structure described above functions as a thermal high-cut filter for the attenuation of the fluctuation of ambient temperature so as to minimize the influence on the samples X, Y, and as a material, a material other than aluminum may be employed. As the block 21, another material can be employed as long as it serves as a thermal bath.

The block 21 constituting this sample holder 2 has two sample housing spaces $S_4$, $S_4$ in an upward opening state, and the sample housing spaces $S_4$, $S_4$ are made openable by demounting a lid 22. Inside of the block 21, a platinum resistance thermometer 8 is embedded, and this thermometer is read by a digital resistance meter 9.

In addition, in the housing space $S_4$, $S_4$, thermoelectric module 1, 1' are disposed; at a detection end of one thermoelectric module 1, a sample X is disposed; and at an detection end of the other thermoelectric module 1', a reference substance (reference sample) Y is disposed, respectively; and further, a thermoelectromotive force difference therebetween is taken out and amplified by a chopper-type amplifier (ultralow noise amplifier) 6 so as to be displayed or registered as a thermoelectromotive force difference by a digital voltmeter 7. The chopper-type amplifier is a direct current amplifier for intermittently converting a direct current signal to an alternating current signal at a predetermined frequency, amplifying the converted signal, and thereafter, phase-discriminating and rectifying and then returning to a direct current, and in order to achieve a heat flow resolution of 1 nW or less, resolution of a voltmeter is enhanced to 1 nV or less.

In such a construction, the embodiment attempts to optimize the thermoelectric module 1 (1') in order to remarkably enhance its sensitivity in comparison with a conventional calorimeter. In general, a commercially available thermoelectric module which is designed for thermoelectric cooling is not optimized for measurement of the quantity of heat as has been already described, a calorimeter employing a thermoelectric module optimized for measurement of the quantity of heat has not been developed yet, and there is no conceptual idea to optimize the module for measurement of the quantity of heat.

Therefore, a condition for thermoelectric module suitable for a calorimeter is theoretically studied, and the module is actually proto-typed so as to enhance an advantageous effect thereof.

The thermoelectric module 1 (1') that is employed as a heat flow sensor, as shown in FIG. 3, is configured so that a P-type thermoelectric element (P-type semiconductor) 16 and an N-type thermoelectric element (N-type semiconductor) 17, which are one pair of thermoelectric elements constituting a thermoelectric module, are connected alternately of π-shape between top and bottom metal plates 14, 15 which are conductive members. In addition, the metal plates 14, 15 and the thermoelectric elements 16, 17 are sandwiched by electric insulating substrates 18, 19.

In a case where this thermoelectric module 1 (1') is employed as a heat flow sensor of a calorimeter, there is a need to enhance a calorimetric sensitivity for obtaining a fine heat flow resolution. However, as in the following study, if an attempt is made to enhance the calorimetric sensitivity to its extremity, an influence due to a thermal noise cannot be ignored and thus from these points of view, the thermoelectric module must be optimized.

For semiconductors 16, 17, Bi—Te-based semiconductors with their large Seebeck coefficients are employed, and are disposed as heat flow sensors between a thermal bath 21 and a sample X and the thermal bath 21 and a reference substance Y shown in FIG. 2.

Next, a deriving process of a heat flow resolution will be described.

In a case where the thermoelectric module 1 (1') is employed as a heat flow sensor of the calorimeter, as shown in FIG. 4, a calorimetric sensitivity (V/W) which is a ratio of a voltage ΔV (V) to be generated when a heat flow Q (W) is applied is derived as follows. Assuming that a Seebeck coefficient of a thermoelectric material is S (V/K), and the number of pairs of the thermoelectric elements 16, 17 is n, the voltage ΔV (V) to be generated when a temperature difference ΔT (K) is generated on each face of the thermoelectric module 1 (1') is obtained as nSΔT (V). Assuming that a thermal conductance between substrates 18 and 19 of the thermoelectric module 1 (1') is K (W/K), the temperature difference ΔT (K) to be generated when the heat flow Q (W) flows in and out of a sample is obtained as Q/K (K). Therefore, the calorimetric sensitivity is represented by the formula below:

Calorimetric sensitivity(V/W) = (1)

$$\frac{\text{Generated voltage } \Delta V(V)}{\text{Heat flow } Q(W)} = \frac{nS}{K}(V/W).$$

Here, as shown in FIG. 5, it is assumed that a cross-sectional area of a P-type thermoelectric element is $A_p$, a length is $L_p$, a cross-sectional area of an N-type thermoelectric element is $A_N$, and a length is $L_N$. Here, although the thermoelectric element is a rectangular cylinder, it may be another rectangular cylinder, a circular cylinder, or an elliptical cylinder or the like. Assuming that thermal conductivity of a P-type semiconductor is $\kappa_p$, and thermal conductivity of an N-type semiconductor is $\kappa_N$, a thermal conductance $K_0$ (W/K) between substrates 18 and 19 of a thermoelectric module, due to one pair of thermoelectric elements (single element pair) 13, is obtained as follows:

$$K_0 = \kappa_P \frac{A_P}{L_P} + \kappa_N \frac{A_N}{L_N} \quad (2)$$

Therefore, a thermal conductance $K_M$ (W/K) between the substrates 18 and 19 of the thermoelectric module 1 (1'), due to n single element pairs 13$_1$, 13$_2$, ..., 13$_n$, shown in FIG. 4, if a thermal resistance of a jointing portion, due to soldering or the like, can be ignored, is represented by the formula below:

$$K_M = nK_0 = n\left(\kappa_P \frac{A_P}{L_P} + \kappa_N \frac{A_N}{L_N}\right) \quad (3)$$

In the conventional thermoelectric module, the above-mentioned thermal conductance $K_M$ was very large in comparison with the thermal conductance $K_A$ due to an atmosphere and a thermoelectric element, convection, or thermal radiation or the like via a reinforcement material such as a material filled between electro-thermal elements and thus the thermal conductance $K_A$ could be ignored; and however, if $K_M$ is decreased in order to enhance the sensitivity to its extremity, a value of $K_A$ cannot be ignored, and must be taken into an account.

In FIG. 6, the passageways of the thermal conductance between both faces 18 and 19 of a thermoelectric element 13 constituting the thermoelectric module 1 (1') and the thermal conductance $K_M$ due to the thermoelectric elements 16, 17 are indicated by the solid line, and the passageway of the thermal conductance $K_A$ that is based on a correlation between a thermal bath, due to gas, and a thermoelectric module is indicated by the dashed line. Since the thermoelectric elements 16, 17 are vulnerable, in the case of reinforcement by filling a resin between the thermoelectric elements 16 and 17 or the like, the thermal conductance of the reinforcement material such as the resin is included in $K_A$.

Therefore, K is represented by the formula below:

$$K = K_M + K_A = n\left(\kappa_P \frac{A_P}{L_P} + \kappa_N \frac{A_N}{L_N}\right) + K_A \quad (4)$$

Hence, by substituting the formula (4) for the formula (1), the calorimetric sensitivity is represented by the formula below:

$$\text{Calorimetric sensitivity}(V/W) = \frac{nS}{K_M + K_A} = \frac{S}{\left(\kappa_P \frac{A_P}{L_P} + \kappa_N \frac{A_N}{L_N}\right) + \frac{K_A}{n}} \quad (5)$$

However, when an attempt is made to measure a thermal noise of a minute heat flow of the order of nW in order to pursue the performance of a thermoelectric module, it was found that the thermal noise cannot be ignored. Namely, it was found to be important to perform optimization including the thermal noise of the thermoelectric module 1 (1'). Assuming that the size of a resistance is R, the Boltzmann constant is κ, and a frequency bandwidth to be measured is Δf, the thermal noise is represented by the formula below:

$$\text{Thermal noise} = \sqrt{4kT\Delta fR}\,(V) \quad (6)$$

Therefore, as shown in FIG. 5, assuming that an electrical resistivity of a P-type semiconductor is $\rho_P$, and an electrical resistivity of an N-type semiconductor is $\rho_N$, an electric resistance $R_M$ of the thermoelectric module 1 (1') made of n pairs of thermoelectric elements 16, 17 is represented by the formula below:

$$R_M = n\left(\rho_P \frac{L_P}{A_P} + \rho_N \frac{L_N}{A_N}\right) \tag{7}$$

Here, it is assumed that the electric resistance of a joint portion, due to soldering, can be ignored in comparison with the electric resistances of the thermoelectric elements 16, 17. Assuming that an absolute temperature of the thermoelectric module 1 (1') is $T_M$, a resistance of lead wires 60 (refer to FIG. 2) between the thermoelectric module 1 (1') and an amplifier 6 is Rw, an absolute temperature of the lead wire 60 is Tw, an equivalent noise resistance of the amplifier 6 is $R_A$, and a standard noise temperature is $T_A$, in the case of the form of FIG. 7 (a) employing two thermoelectric modules 1, 1', a noise (V) due to these modules is obtained as follows:

$$\text{Noise} = \sqrt{4k\Delta f(2T_M R_M + T_A R_A + T_W R_W)} = \tag{8}$$
$$\sqrt{4k\Delta f\left(2T_M n\left(\rho_P \frac{L_P}{A_P} + \rho_N \frac{L_N}{A_N}\right) + T_A R_A + T_W R_W\right)}$$

Also, in the case of the form of FIG. 7 (b) employing one thermoelectric module 1, it is represented as follows:

$$\text{Noise} = \sqrt{4k\Delta f(T_M R_M + T_A R_A + T_W R_W)} = \tag{9}$$
$$\sqrt{4k\Delta f\left(T_M n\left(\rho_P \frac{L_P}{A_P} + \rho_N \frac{L_N}{A_N}\right) + T_A R_A + T_W R_W\right)}$$

Therefore, a heat flow resolution F (a minimum heat flow can be measured) is obtained as follows:

$$\text{Heat flow resolution (W)} = \frac{\text{Noise(V)}}{\text{Calorimetric sensitivity(V/W)}} \tag{10}$$
$$= F(L/A, n)$$
$$= \frac{K_M + K_A}{nS} \sqrt{4k\Delta f(2T_M R_M + T_A R_A + T_W R_W)}$$
$$= \frac{1}{S}\left[\left(\kappa_P \frac{A_P}{L_P} + \kappa_N \frac{A_N}{L_N}\right) + \frac{K_A}{n}\right]\sqrt{4k\Delta f\left(2T_M n\left(\rho_P \frac{L_P}{A_P} + \rho_N \frac{L_N}{A_N}\right) + T_A R_A + T_W R_W\right)}$$

(In the case of two pieces), $$= \frac{K_M + K_A}{nS} \sqrt{4k\Delta f(T_M R_M + T_A R_A + T_W R_W)} \tag{11}$$
$$= \frac{1}{S}\left[\left(\kappa_P \frac{A_P}{L_P} + \kappa_N \frac{A_N}{L_N}\right) + \frac{K_A}{n}\right]\sqrt{4k\Delta f\left(T_M n\left(\rho_P \frac{L_P}{A_P} + \rho_N \frac{L_N}{A_N}\right) + T_A R_A + T_W R_W\right)}$$

(In the case of one piece),

The formula (10) is established in the case of two thermoelectric modules, and the formula (11) is established in the case of one thermoelectric module, assuming that the number of thermoelectric modules is x, it can be represented as follows:

$$\text{Noise} = \sqrt{4k\Delta f(xT_M R_M + T_A R_A + T_W R_W)} = \sqrt{4k\Delta f\left(xT_M n\left(\rho_P \frac{L_P}{A_P} + \rho_N \frac{L_N}{A_N}\right) + T_A R_A + T_W R_W\right)} \tag{12}$$

$$\text{Heat flow resolution (W)} = F(L/A, n) \tag{13}$$
$$= \frac{K_M + K_A}{nS} \sqrt{4k\Delta f(xT_M R_M + T_A R_A + T_W R_W)}$$
$$= \frac{1}{S}\left[\left(\kappa_P \frac{A_P}{L_P} + \kappa_N \frac{A_N}{L_N}\right) + \frac{K_A}{n}\right]\sqrt{4k\Delta f\left(xT_M n\left(\rho_P \frac{L_P}{A_P} + \rho_N \frac{L_N}{A_N}\right) + T_A R_A + T_W R_W\right)}$$

Here, the smaller the heat flow resolution is, the better the performance is.

As is evident from this result, if the L/A ratio is increased, the heat flow resolution is decreased while $K_O$ is larger than $K_A/n$, whereas if $K_O$ is smaller than $k_A/n$, the heat flow resolution increases. Also, if the number n of the pairs is increased, the heat flow resolution increases, whereas an influence of $K_A$ can be reduced.

In the embodiment, a program for executing a function (Formula (10), Formula (11), or Formula (13) mentioned above) which computes a heat flow resolution while an L/A ratio (L: length and A: cross-sectional area) of a thermoelectric element constituting a thermoelectric module 1 is written as a design program into a computer memory; a realistic value is assigned to a required constant; and thereafter, values of the L/A ratio and the number n of the pairs is appropriately input through an interface or repeatedly input in program to thereby cause a CPU to compute the heat flow resolution. In a case where the abovementioned program is supplied to a computer via a recording medium, the program that is recorded in a recording medium also comes under the present invention. As the recording medium, for example, there can be employed: a flexible disk; a hard disk; a solid state disk; an optical disk; an optical magnetic disk; a CD-ROM; a CD-R, a blue-ray disk; a magnetic tape; a nonvolatile memory card; and a ROM. Also, the present invention includes a case in which an OS or the like operating on the computer performs part or all of actual processing on the basis of a command of a program code of a program read out by the computer, and a function of the present invention is achieved by that processing.

In the embodiment, actual computation is performed by employing the following values for the respective parameters.

Seebeck coefficient S=0.40 mVK$^{-1}$
Thermal conductivity $\kappa p=\kappa_N$=1.35 Wm$^{-1}$K$^{-1}$
Electrical resistivity $\rho_P=\rho_N$=10.2 μΩm
Amplifier equivalent noise resistance $R_A$=20Ω
Lead wire resistance $R_W$=0.15Ω
Thermal conductance $K_A$=5×10$^{-4}$ WK$^{-1}$
Temperature T=273K Also, the following is a specific embodiment of a thermoelectric element and a module Thermoelectric element size (L/A≈50): L=1.3 mm and A=(0.16 mm)$^2$
Module size (n=32): 3 mm×3 m×2 mm However, the parameter range in which 10 nW or less is obtained is wider than the above, and the following is included in at least that range.

Seebeck coefficient S=0.01 to 1 mVK$^{-1}$
Thermal conductivity $\kappa p=\kappa_N$=1 to 400 Wm$^{-1}$K$^{-1}$
Electrical resistivity $\rho_P=\rho_N$=1×10$^{-8}$ to 4×10$^{-2}$ Ωm
Amplifier equivalent noise resistance $R_A$=1×10$^{-2}$ to 4×10$^6$Ω
Amplifier frequency bandwidth Δf=1×10$^{-2}$ to 4×10$^3$ Hz
Lead wire resistance $R_W$=1×10$^{-2}$ to 4×10$^6$Ω
Thermal conductance $K_A$=1×10$^{-8}$ to 0.7 WK$^{-1}$
Temperature T=30 K to 1,300 K Also, in respect of a module optimal size, although the smaller the module is, the better it is, from the view point of a response speed, a sample is hardly placed and thus the order of 3 to 6 mm in vertical and horizontal direction is appropriate. The thinner the top substrate is, the better it is.

In respect of a height, although there is no optimal size in particular other than a face with a strength, if a gap between top and bottom substrates is narrow, the thermal conductance $K_A$ due to an atmosphere increases, and the calorimetric sensitivity decreases and thus it is desirable that the height be 1 mm or more.

FIG. 8 graphically depicts dependency of a calorimetric sensitivity relative to an L/A ratio and the number n of the pairs when a calorimetric sensitivity (V/W) is computed by inputting realistic values into the thermal conductivity κ of a material for Bi—Te-based thermoelectric elements 16, 17, a resistivity ρ, thermal conduction by gas $K_A$, a lead wire resistance $R_W$, and an amplifier equivalent noise resistance $R_A$ or the like.

Also, FIG. 9 graphically depicts dependency of a noise (V) relative to an L/A ratio and the number n of the pairs similarly.

As is evident from these graphs and the formulas (5), (8), (9) or the like, if the L/A ratio is increased, the calorimetric sensitivity (V/W) increases, whereas the noise (V) also increases. In respect of the number n of the pairs, if n is increased, the calorimetric sensitivity (V/W) increases, whereas the noise (V) increases. If the number n of the pairs are too small, the thermal conductance $K_M$ is smaller than the thermal conductance $K_A$, and it was found that the thermal conductance $K_A$ is dominant, and the calorimetric sensitivity (V/W) reaches the ice.

Also, if the number n of the pairs or the L/A ratio is decreases, the noise decreases; and however, in the configuration of FIG. 7 (a), if $2R_M$ is smaller than $R_A$-$R_W$, and in the configuration of FIG. 7 (b), if $R_M$ is smaller than $R_A$-$R_W$, it was found that almost no improvement is obtained. Therefore, in the configuration of FIG. 7 (a), when $2R_M \geq R_A$-$R_W$ and in the configuration of FIG. 7 (b), when $R_M \geq R_A$-$R^W$ or when x thermoelectric modules are employed, $xR_M \geq R_A$-$R_W$ can be one of the preferred conditions. In respect of the electric resistance $R_M$ of this thermoelectric module, as an appropriate example, there can be respectively exemplified: $2R_M \approx R_A$-$R^W$ in the case of FIG. 7 (a); $R_M \approx R_A$-$R^W$ in the case of FIG. 7 (b); and $xR_M \approx R_A$-$R^W$ in the case of the number x.

From the foregoing description, in the thermoelectric modules 1, 1', samples X, Y are provided so that absorption and release of heat is carried out via the thermoelectric modules 1, 1' for the sample holder 2 that is a temperature-controlled thermal bath; and for the sake of taking out a voltage according to a heat flow flowing through the samples 1, 1' at a time of the endothermic or exothermic process, at the predetermined positions of the thermoelectric module 1, 1', the thermoelectric modules 1, 1' are so configured that one pair of a P-type thermoelectric element 16 and an N-type thermoelectric element 17 are connected in n pairs between substrates 18 and 19 so that the P-type thermoelectric element 16 and the N-type thermoelectric element 17 are arranged alternately in π-shape to thereby form a structure in which the calorimetric sensitivity of the thermoelectric modules 1, 1' corresponds to: the thermal conductance $K_A$ due to the atmosphere occupied by the thermoelectric modules 1, 1' or thermal conduction via a reinforcement member such as a material filled between the thermoelectric elements 16, 17 constituting the thermoelectric modules 1, 1', convection of the atmosphere, and thermal radiation through the atmosphere; and the thermal conductance $K_M$ between the substrates 18 and 19 of the thermoelectric modules 1, 1', and the noise is based on the electric resistance of the thermoelectric modules 1, 1', the calorimetric sensitivity and the noise depend on the L/A ratio (L: length and A: cross-sectional area) of the thermoelectric elements 16, 17 constituting the thermoelectric modules 1, 1' and the number n of pairs of the thermoelectric elements. In addition, it was found that just fitted values of the L/A ratio and the number n of the pairs exist, and these values can be easily appropriately selected according to the embodiment.

FIG. 10 graphically depicts dependency of a heat flow resolution (W) relative to an L/A ratio and the number n of the pairs on the basis of the formula (10), wherein the number n of the pairs and L/A ratio of a thermoelectric module type heat flow sensor suitable for a calorimeter can be obtained by assigning the thermal conductivity κ and resistivity ρ of thermoelectric material, thermal conductance $K_A$ due to gas or the like, lead wire resistance Rw, and an amplifier equivalent noise resistance or the like.

These graphic functions of FIG. 8, FIG. 9, and FIG. 10 are provided as part of the abovementioned design programs, and the computer displays these graphs on the display or monitor by executing the programs or can output them as print data or image data to a printer or a variety of storages in response to a request.

Referring to the illustrative example, for instance, the saturation values of a heat flow resolution when an L/A ratio is varied under the number n of the pairs=(8, 32) are respectively on the order of (0.22 nW and 0.18 nW), and if the resolution substantially saturates, the L/A ratio is arbitrarily selected and thus the L/A ratio can be freely selected. Speaking of the example of the FIG. 10 (a), if 100 mm$^{-1}$ or more is obtained, the value of the heat flow resolution is in a substantially saturated state and thus the L/A ratio can be freely selected. Even if the L/A ratio is out of the saturated region, for example, in FIG. 10 (b), if the L/A ratio is on the order of 50 times of the saturation value, the heat flow resolution is on the order of 10 nW; if the L/A ratio is within the order of 10 times, the heat flow resolution is on the order of 2 nW, which is good; and moreover, if the L/A ratio is 10 mm$^{-1}$ or more, the heat flow resolution can be freely selected; and therefore, the degree of freedom of design is improved more remarkably. If the L/A ratio is within the order of 5 times of the saturation value, the heat flow radiation is on the order of 1 nW, which is further remarkably improved. For example, from the viewpoint of a mechanical strength, when there is a need to retain the L/A ratio to 100 mm$^{-1}$ or less as well, the L/A ratio can be sufficiently widely selected while 10 mm$^{-1}$ is defined as a lower limit.

However, in view of the fact that the heat flow resolution is impaired when n=1 to 2 from the FIG. 10 (b), and that the heat flow resolution is impaired when the L/A ratio is less than 6 mm$^{-1}$ from FIG. 10 (a) and FIG. 10 (b), it is preferable that the L/A ratio set to be 6 mm$^{-1}$ or more and the number n of the pairs set to be 4 or more.

Further speaking, as seen from FIG. 8, the calorimetric sensitivity saturates when n=1,024 or more; as seen from FIG. 9, noise increases when n=1,024 or more; and from FIG. 10 (b), the heat flow resolution is impaired when n=1,024. Also, if the L/A ratio is in excess of 1,000 mm$^{-1}$, the mechanical strength weakens. Hence, it is preferable that the L/A ratio set to be 6 to 1,000 mm$^{-1}$ or less and the number n of the pairs set to be 4 to 512 or less.

However, if the number n of the pairs is up to 512, from a condition that it is better that the thermal conduction $K_M$ of the thermoelectric module is larger than thermal conduction $K_A$ such as air ($K_M \geq K_A$), if an upper limit of the number of the pairs is limited, $K_M$ cannot be increased and thus when the L/A ratio is large, there is a possibility that $K_M \geq K_A$ is not met.

For example, in a proto-typed module, when the L/A ratio is 50 and the number of the pairs is 64, it was experimentally verified that $K_M \approx K_A$ is obtained and thus in a case where the L/A ratio is 100, when the number of the pairs is 128, and in the case where the L/A ratio is 200, when the number of the pairs is 256, it is estimated that $K_M \approx K_A$ is obtained, respectively. However, depending on a material, there may be a case in which $K_M \geq K_A$ is not met; and therefore, this does not mean the exclusion of the fact that the number n of the pairs is larger than 512 in the range that meets $K_M \geq K_A$.

Incidentally, FIG. 11 shows a noise value under a constant temperature of a ultrahigh sensitive DSC using a proto-typed thermoelectric module, and FIG. 12 shows a value of a heat flow resolution under a constant temperature of the ultrahigh sensitive DSC using the proto-typed thermoelectric module. In FIG. 8 to FIG. 10, the positions designated by reference numerals 30, 31 indicate computational values in a case where a condition similar to the prototyping condition in FIG. 11 and FIG. 12 is given. In the data shown in FIG. 11, it can be verified that, in any case also, the heat flow resolution is enhanced up to the order of 5 nW or less and further in the data shown in FIG. 12, it can be verified that in any case also, the heat flow resolution is enhanced up to the order of 5 nW or less. In particular, in the case of prototyping of this thermoelectric module, when the number n of the pairs=32 and L/A ratio=50 mm$^{-1}$ are employed, it was verified that the heat flow resolution can be 0.24 nW, which is the best. This value is ¼,000 of the conventional general calorimeter resolution, and in comparison with a calorimeter with the highest precision, the level of ultrahigh performance is achieved as ¹⁄₄₀. Also, it could be experimentally verified that at least a range of −30 degrees Centigrade and 170 degrees Centigrade is an appropriate operating temperature. Of course, in a case where the L/A ratio is 50 mm$^{-1}$ or more, and the number n of the pairs are 32 or more as well, the performance conforming thereto can be anticipated. In particular, when the number n of the pairs is 64, the advantageous effect conforming to the above description is attained, and further, on the basis of the study of FIG. 10 (b) described above, setting the L/A ratio to be 50 to 1,000 mm$^{-1}$ and the number n of the pairs to be 32 to 256 or less can also be in an effective range.

However, in view of the fact that, in the heat flowmeter, a sample must be placed on an electronic module, it is desirable that the L/A ratio be 500 mm$^{-1}$ or less or 200 mm$^{-1}$ or less, which is slightly larger.

It can be verified that the the number n of the pairs are flexibly selected in a range in which a required heat flow resolution can be obtained, and an optimal number n of the pairs can be selected from the viewpoint of costs or strength in view of a good balance with the L/A ratio.

Incidentally, as seen from FIG. 10, if the number n of the pairs increases more (for example, n=64 and 128), and the L/A ratio is 100 mm$^{-1}$ or more, it is also readable that there is a possibility that the heat flow resolution can be further enhanced.

A reason why the resolution has been thus remarkably enhanced is that, as constituting a calorimeter in which the samples X, Y are provided via the thermoelectric module 1 (1') having: the metal plates 14, 15 electrically wiring the thermoelectric elements 16, 17 in the temperature-controlled thermal bath 21; and the substrates 18, 19 sandwiching the thermoelectric elements 16, 17 and the metal plates 14, 15 therebetween, and temperatures of the samples X, Y are detected at the predetermined position of the thermoelectric modules 1 (1'), in consideration of the thermal conductance $K_A$ due to: the atmosphere around the thermoelectric modules 1 (1') or thermal conduction via a reinforcement member such as a material filled between the thermoelectric elements 16, 17 constituting the thermoelectric modules 1

(1'); convection of atmosphere; and thermal radiation through atmosphere, and the thermal conductance $K_M$ (thermal conductance between the substrates 18 and 19) of the thermoelectric module 1 (1'), and the thermal noise, the function F (L/A and n) of the heat flow resolution (=noise/ calorimetric sensitivity) is defined while the L/A ratio (L: length and A: cross-sectional area) and the number n of pairs of the thermoelectric elements 16, 17 constituting the thermoelectric pairs 13 of the modules 1 (1') are employed as variables, and based on this function F, the L/A ratio and the number n of the pairs are selected.

Incidentally, FIG. 13 illustrates baseline data due to a differential scanning calorimeter according to the present invention. In the figure, a baseline of a heat flow is measured at a scanning rate of 0.1 K/min in a state in which there is neither sample nor reference sample.

Also, FIG. 14 is an example of noise due to the differential scanning calorimeter according to the present invention. Relative to FIG. 13 in which a baseline of a heat flow is measured at a scanning rate of 0.1K/min in a state in which there is neither sample nor reference sample, the baseline is fitted by a quadratic curve, and a residual difference with the quadratic curve is shown.

Further, FIG. 15 shows a measurement example due to the differential scanning calorimeter according to the present invention. A heat flow in a phase transition from the crystalline phase of straight-chain hydrocarbon n-tetracosane ($C_{24}H_{50}$) to the rotational phase and in a phase transition from the rotational phase to the liquid phase was measured. Measurement was carried out by employing an extremely small amount of sample of 13 μg. In order to indicate sensitivity, a heat flow curve at a temperature immediately above the phase transition from the rotational phase to the liquid phase was shown in an enlarged manner. It is evident that the magnitude of noise is 1 nW or less.

Although one embodiment of the present invention has been described hereinabove, the present invention can be applied to an power compensation DSC and an isothermal calorimeter or the like as well as a heat flux DSC, and can be effectively applied to a case of detecting a temperature of a sample which is a measurement target by non-differential method without being limitative to a case of constituting a differential scanning calorimeter for detecting a temperature difference between a sample and a reference substance.

Also, in a case where a sample is large in size, a thermoelectric module can be divided into a plurality of thermoelectric modules. In that case, it is sufficient if the number n of the pairs be a sum of the number of pairs in the plurality of thermoelectric modules thus divided.

Further, if a calorimeter is provided with depressurization means 200 (refer to FIG. 2) for depressurizing the atmosphere occupied by a thermoelectric module, an influence due to a thermal conductance $K_A$, which is also due to thermal conduction or convection of gas, is reduced, and a heat flow resolution can be enhanced more effectively.

Incidentally, in respect of the above descriptive matters, although there is reduced an advantageous effect of improving a heat flow resolution, there is attained another advantageous effect such as enhancing a mechanical strength or easy manufacturing; and therefore, these descriptive matters are not always limitative to applying of an entire thermoelectric module which constitutes a calorimeter, and can be adapted to part of the thermoelectric module, In addition, a specific construction or the like of each constituent element, such as constituting a thermopile by employing a thermoelectric element other than a thermoelectric module, is not limited to only the embodiment described above, various modifications can occur without departing from the spirit of the present invention.

Incidentally, in the foregoing embodiment, a Bi—Te-based semiconductor ($Bi_2Te_3$-base) was employed for a thermoelectric material, the thermoelectric material is not limitative thereto. For example, there can be exemplified Pb—Te-base and Si—Ge-base or the like.

FIGS. 17 and 18 respectively depict graphs indicating dependency of a heat flow resolution relative to an L/A ratio and the number n of pairs when these thermoelectric materials are employed, at a temperature of 300 K or its proximity. From these graphs, although the calorimetric sensitivity is different depending on each material, the ranges of the values of highly sensitive L/A ratio and the number n of the pairs are almost identical to each other, and it is found that the values of a just fitted L/A ratio and the number n of the pairs exist for the respective materials, and that these values can be easily appropriately selected and also the number n of the pairs and L/A ratio suitable for a calorimeter can be obtained.

Further, although no data is exemplified, as other thermoelectric materials, there can be exemplified: a telluride-based material such as $AgSbTe_2$, $AgSbTe_2$—GeTe; a silicide-based material such as $CrSi_2$, MnSi, $Mg_2Si_{0.7}Sn_{0.3}$; a Skutterudite-based material such as CoSi; half whistler such as $(Ti_{0.3}Zr_{0.7})$ NiSn; a boron compound-based material such as $CaB_6$, $SrB_6$; a layered cobalt oxide-based material such as $Na_xCoO_2$; a titanium oxide-based material such as $Sr_3Ti_2O_7$; a zinc antimony-based material; a cluster solid body; a zinc oxide-based material; a natural ultra-lattice-based material; an amorphous, artificial ultra-lattice-based material or the like; and as metals, there can be exemplified chromel, alumel, and constantan or the like.

Also, the heat flow resolution varies depending on the temperature $T_M$. For example, FIG. 19 to FIG. 21 show graphs depicting dependency of the heat flow resolution relative to an L/A ratio and the number n of pairs when temperature TM=175K, 338K, 520K in a case where $Bi_2Te_3$-base is employed as a thermoelectric material. In this case, the sensitivity when $T_M$=520K is impaired.

Incidentally, in order to search for a reasonable range of the above mentioned parameters, while parameters of a proto-typed module employing a $Bi_2Te_3$-based material is employed as standard, FIG. 22 to FIG. 37 each show an area in which 10 nW or less is obtained, by employing values such as Seebeck coefficient S=0.40 $mVK^{-1}$, thermal conductivity $\kappa_p=\kappa_N$=1.35 $Wm^{-1}K^{-1}$, electrical resistivity $\rho_p=\rho_N$=10.2 μΩm, amplifier equivalent noise resistance $R_A$=20Ω, lead wire resistance $R_W$=0.15Ω, thermal conductance $K_A$=5×$10^{-4}$ $WK^{-1}$, and temperature T=273K. In that case, only one standard condition is varied for the sake of search without simultaneously varying a plurality of parameters conveniently.

INDUSTRIAL APPLICABILITY

According to the present invention described in detail hereinabove, it becomes possible to remarkably enhance a heat flow resolution of a calorimeter up to 10 nW or less, preferably 5 nW or less, and further preferably 1 nW or less in comparison with the prior art without employing a complicated structure for a thermoelectric element by appropriately handing a thermal conductance due to thermal conduction, convection, and thermal radiation of gas or the like which cannot be ignored when an attempt is made to form a calorimeter with an ultrahigh sensitivity or a thermal noise of a thermoelectric module. In addition, by substantiating such a high performance calorimeter, even if a temperature scanning rate is low, a sufficient thermoelectromotive force can be obtained from a thermoelectric module, a minute heat anomaly such as thermal denaturing of protein can be precisely measured, which is applicable to and is effective for use in a variety of measurement objects such as biological samples or stratum corneum, liquid crystals.

DESCRIPTION OF REFERENCE NUMERALS

21 . . . Thermal bath
1, 1' . . . Thermoelectric module
n . . . number of pairs of thermoelectric elements constituting thermoelectric module
K . . . Thermal conductance between substrates 18 and 19 of thermoelectric module
$K_A$ . . . Thermal conductance due to thermal conduction, convection, and thermal radiation

The invention claimed is:

1. A calorimeter, comprising:
a thermoelectric module in a temperature-controlled thermal bath, the calorimeter being configured such that heat can flow into and out of a sample via the thermoelectric module, the thermoelectric module comprising a pair of a P-type thermoelectric element and an N-type thermoelectric element disposed between substrates, the pair of the P-type thermoelectric element and the N-type thermoelectric element being connected in n pairs so that the P-type thermoelectric element and the N-type thermoelectric element are arranged alternately in a π-shape; and
a chopper-type amplifier connected to the thermoelectric module through lead wires,
wherein a voltage is taken out according to the heat flow going in and out of the sample at a time of endothermic or exothermic process, at a predetermined position of the thermoelectric module,
wherein the calorimeter is configured to take out a thermoelectromotive force which includes a noise based on an electric resistance of the thermoelectric module and is generated at the thermoelectric module by the heat flow going in and out of the sample, and amplify the thermoelectromotive force with the chopper-type amplifier connected to the thermoelectric module through the lead wires, and
wherein an L/A ratio (L: length and A: cross-sectional area) of the thermoelectric element constituting the thermoelectric module and the number n of the pairs of the thermoelectric elements is set so that:
the L/A ratio is 6 mm$^{-1}$ or more;
the number n of the pairs is in a range of 4 or more;
a relationship between a thermal conductance $K_M$ between the substrates of the thermoelectric module which depends on the L/A ratio and the number n of the pairs, and a thermal conductance $K_A$ due to conduction, convection, and thermal radiation depending on a correlation of the thermal bath and the thermoelectric module, is $K_M \geq K_A$; and
a relationship of $xR_M \geq R_A - R_W$ is established among an electric resistance $R_M$ of the thermoelectric module, the number x of the thermoelectric modules, an equivalent noise resistance $R_A$ of the chopper-type amplifier, and a resistance $R_W$ of the lead wire.

2. The calorimeter according to claim 1, wherein the L/A ratio and the number n of the pairs are selected so that a heat flow resolution (noise/calorimetric sensitivity) is within 50 times to 10 times of a saturation value when the L/A ratio is varied under a predetermined number n of the pairs.

3. The calorimeter according to claim 1, wherein the L/A ratio and the number n of the pairs are selected so that a heat flow resolution (noise/calorimetric sensitivity) is 10 nW or less.

4. The calorimeter according to claim 1, wherein the L/A ratio and the number n of the pairs are selected so that a heat flow resolution (noise/calorimetric sensitivity) is 5 nW or less.

5. The calorimeter according to claim 1, wherein the L/A ratio and the number n of the pairs are selected so that a heat flow resolution (noise/calorimetric sensitivity) is 1 nW or less.

* * * * *